US012642599B2

(12) United States Patent
Zhuang

(10) Patent No.: US 12,642,599 B2
(45) Date of Patent: Jun. 2, 2026

(54) NAVIGATION OPERATION DEVICES, METHODS FOR NAVIGATION AND ULTRASOUND IMAGING SYSTEMS

(71) Applicant: WUHAN UNITED IMAGING HEALTHCARE CO., LTD., Wuhan (CN)

(72) Inventor: Rui Zhuang, Wuhan (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 241 days.

(21) Appl. No.: 18/518,982

(22) Filed: Nov. 25, 2023

(65) Prior Publication Data

US 2024/0173083 A1      May 30, 2024

(30) Foreign Application Priority Data

Nov. 25, 2022    (CN) .......................... 202211488263.2
Nov. 25, 2022    (CN) .......................... 202223137669.4

(51) Int. Cl.
*A61B 34/20*        (2016.01)
*A61B 8/00*         (2006.01)
*G06F 3/01*         (2006.01)

(52) U.S. Cl.
CPC ............... *A61B 34/20* (2016.02); *A61B 8/46* (2013.01); *G06F 3/016* (2013.01)

(58) Field of Classification Search
CPC ... A61B 34/20; A61B 90/37; A61B 2090/378; A61B 34/25; A61B 34/76; A61B 2034/742; A61B 5/7475; A61B 2017/00106; A61B 2090/3925; A61B 2034/744; A61B 2034/743; A61B 6/4405; A61B 2017/3413; A61B 8/46; A61B 6/548
See application file for complete search history.

(56) References Cited

U.S. PATENT DOCUMENTS

| | | | |
|---|---|---|---|
| 2005/0007347 A1* | 1/2005 | Anastas | .............. G06F 3/03549 |
| | | | 345/167 |
| 2009/0063118 A1 | 3/2009 | Dachille et al. | |
| 2009/0195514 A1* | 8/2009 | Glynn | ................... A61B 8/565 |
| | | | 345/173 |
| 2010/0286522 A1 | 11/2010 | Beach et al. | |

(Continued)

FOREIGN PATENT DOCUMENTS

EP        1857912 A1    11/2007

OTHER PUBLICATIONS

First Office Action in Chinese Application No. 202211488263.2 mailed on Apr. 21, 2025, 26 pages.

*Primary Examiner* — Gerald Johnson
(74) *Attorney, Agent, or Firm* — METIS IP LLC

(57)            ABSTRACT
The embodiments of the present disclosure provide an ultrasound imaging system including a navigation operation device. The navigation operation device may include a supporting component, a navigation operation component, and a feedback assembly. The navigation operation component may be configured to perform a navigation operation on a display screen; and the feedback assembly may be configured to drive, based on the navigation operation, the navigation operation component to provide a feedback on the navigation operation.

20 Claims, 15 Drawing Sheets

(56) References Cited

U.S. PATENT DOCUMENTS

| | | | |
|---|---|---|---|
| 2019/0231430 A1* | 8/2019 | Friman | .................. A61B 90/36 |
| 2021/0059636 A1 | 3/2021 | Durfee et al. | |
| 2021/0204880 A1 | 7/2021 | Cedrone et al. | |
| 2024/0173083 A1 | 5/2024 | Zhuang | |

* cited by examiner

100

200

Supporting component
210

Navigation operation
component
220

Feedback assembly
230

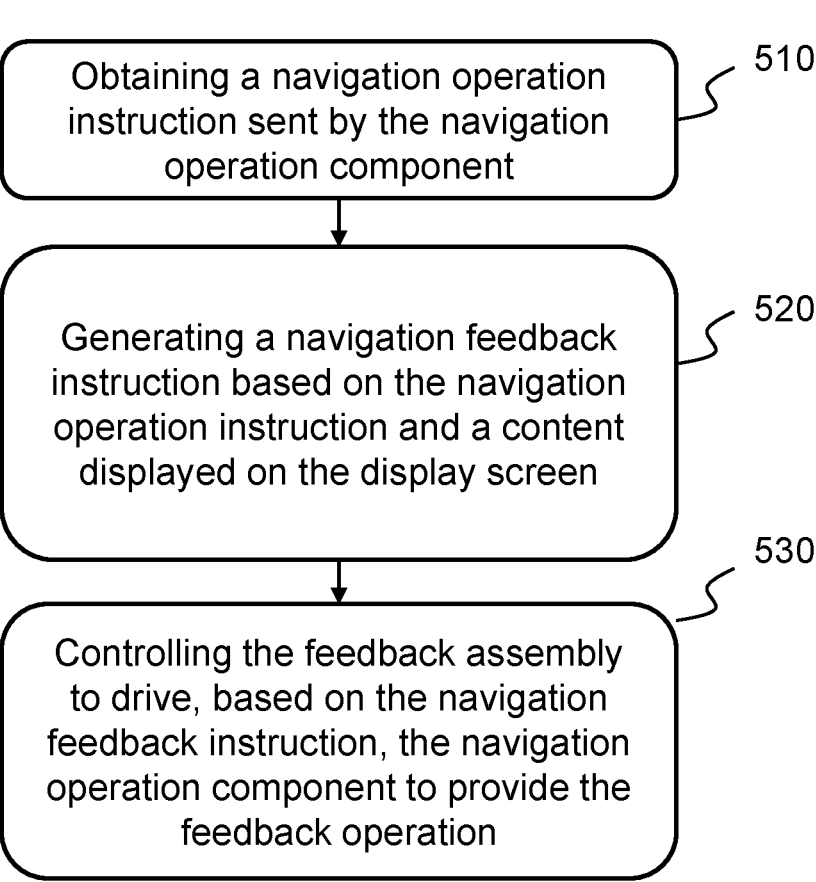

Obtaining a navigation operation instruction sent by the navigation operation component — 510

Generating a navigation feedback instruction based on the navigation operation instruction and a content displayed on the display screen — 520

Controlling the feedback assembly to drive, based on the navigation feedback instruction, the navigation operation component to provide the feedback operation — 530

First navigation
operation device <u>810</u>

Second navigation
operation device <u>820</u>

Driving component
<u>830</u>

FIG. 8

NAVIGATION OPERATION DEVICES, METHODS FOR NAVIGATION AND ULTRASOUND IMAGING SYSTEMS

CROSS-REFERENCE TO RELATED APPLICATION

This application claims priority of Chinese Patent Application No. 202211488263.2 filled on Nov. 25, 2022, and Chinese Patent Application No. 202223137669.4 filled on Nov. 25, 2022, the contents of each of which are entirely incorporated herein by reference.

TECHNICAL FIELD

The present disclosure relates to the technical field of imaging system, and in particular to, a navigation operation device and a navigation operation system for an ultrasound imaging system.

BACKGROUND

In imaging devices such as an ultrasound imaging device, a trackball mouse has become a widely used input device due to its special advantages. The trackball mouse has a unique structural design, and users do not need to move the entire mouse when using. They just rotate a trackball on the mouse, and may freely control a cursor movement on a display screen, which not only saves a use space, but also greatly reduces a wrist fatigue of the user. However, the traditional trackball mouse has a single function and can only be used as a mouse input device, which in turn leads to a limited application.

Accordingly, it is desired to provide a control device and a navigation device for an ultrasound imaging system to extend functions and applications.

SUMMARY

One of the embodiments of the present disclosure provides an ultrasound imaging system. The system may include a navigation operation device including a supporting component, a navigation operation component configured to perform a navigation operation on a display screen; and a feedback assembly may be configured to drive, based on the navigation operation, the navigation operation component to provide a feedback on the navigation operation.

In some embodiments, the feedback assembly may include a driving component, the driving component being configured to drive the navigation operation component to provide the feedback according to the navigation operation.

In some embodiments, the driving component may include at least two motors and a driving circuit. The motors may include a rotating shaft, and the driving circuit may be configured to drive the at least two motors to rotate around the rotating shaft, the rotating shaft being connected with the navigation operation component.

In some embodiments, the feedback assembly may include a controller, the controller may be configured to: receive a navigation operation instruction sent by the navigation operation component, wherein the navigation operation instruction includes navigation information indicating that a navigation cursor moves on the display screen of the ultrasound imaging system; generate a navigation feedback instruction based on the navigation information and a content displayed on the display screen; and control the feedback assembly to drive, based on the navigation feedback instruction, the navigation operation component to provide a feedback operation.

In some embodiments, the feedback operation may include at least one of a vibration feedback, a sound feedback, a movement feedback, or a force feedback.

In some embodiments, the navigation information may be parsed to determine a moving track of the navigation cursor on the display screen by analyzing the navigation information; generate based on the moving track and the content, the navigation feedback instruction.

In some embodiments, the content displayed may include a region of interest and a region of non-interest, and the navigation feedback instruction may be generated based on motion information of the moving track in the region of interest and the region of non-interest.

In some embodiments, a reference line may be obtained; in response to that the moving track passes the reference line, a first navigation feedback instruction may be generated. The first navigation feedback instruction may be used to instruct the navigation operation device to generate the feedback operation indicating that the moving track passes the reference line.

In some embodiments, whether the moving track is far from the region of interest may be determined based on a position of each track point in the moving track; in response to that the moving track is far from the region of interest, a second navigation feedback instruction may be generated. The second navigation feedback instruction may be used to instruct the navigation operation device to generate the feedback operation indicating that the moving track is far from the region of interest.

In some embodiments, a target direction of a position of the track point relative to the region of interest may be obtained; and the second navigation feedback instruction indicating a reverse movement of the navigation operation device relative to the target direction may be obtained.

In some embodiments, a speed of the reverse movement of the navigation operation device relative to the target direction increases as the moving track moves far from the region of interest.

In some embodiments, an end position of the moving track in the content displayed may be determined; motion information of the displayed object at the end position in the displayed content may be obtained; a third navigation feedback instruction may be generated based on the motion information. The third navigation feedback instruction may be used to instruct the navigation operation device to generate a motion consistent with the motion information of the displayed object.

In some embodiments, the region of interest may be determined based on the navigation information; a fourth navigation feedback instruction may be generated based on based on a feature of the region of interest. The fourth navigation feedback instruction may be used to instruct the navigation operation device to generate the feedback operation indicating the feature of the region of interest.

In some embodiments, the feedback on the navigation operation may include providing a resistance force or a driving force on the navigation operation component for adjusting a previous resistance force of the navigation operation.

In some embodiments, the driving force may be equal to the previous resistance force of the navigation operation.

In some embodiments, the system may further include another navigation operation device configured to perform a first navigation operation on another display screen. The feedback assembly may be configured to cause, based on the first navigation operation, the navigation operation component to perform a second navigation operation on the display screen. Navigation information of the first navigation operation on the another display screen may be the same as navigation information of the second navigation operation on the display screen.

One embodiment of the present disclosure provides a navigation operation device including: a supporting component, a navigation operation component, and a driving component. The navigation operation component and the driving component may be installed on the supporting component; and the navigation operation component moves driven by the driving component, so as to perform a navigation operation on a display screen of an ultrasonic imaging system.

In some embodiments, the navigation operation component may include a trackball.

In some embodiments, the driving component may include one or more motors and a driving circuit. The one or more motors may include one or more rotating shafts, the one or more rotating shafts being disposed in contact with the navigation operation component, the driving circuit may be connected to the one or more motors; and the driving circuit may be configured to drive the one or more motors to rotate.

In some embodiments, the one or more motors may include a first motor and a second motor. A rotating shaft of the first motor may be disposed in contact with the navigation operation component along a first direction, and a rotating shaft of the second motor may be disposed in contact with the navigation operation component along a second direction. The first direction and the second direction may be different directions.

In some embodiments, the navigation operation device may further include a magnetic field sensor disposed on the motor. The magnetic field sensor may be used to detect a rotation state of the one or more motors.

One of the embodiments of the present a method for navigation implemented by an ultrasound imaging system including a navigation operation device, the method including: receiving a navigation operation instruction sent by a navigation operation component of the navigation operation device, the navigation operation instruction including navigation information indicating that a navigation cursor moves on a display screen of the ultrasound imaging system; generating a navigation feedback instruction based on the navigation information; and controlling a feedback assembly of the navigation operation device to drive, based on the navigation feedback instruction, the navigation operation component to provide a feedback operation.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which the same reference numbers represent the same structures, and wherein:

FIG. 2 is a schematic diagram illustrating a control device for an ultrasound imaging system according to some embodiments of the present disclosure;

FIG. 5 is a flowchart illustrating an exemplary process for feedback for a navigation operation according to some embodiments of the present disclosure;

FIG. 8 is a schematic diagram illustrating a navigation operation system according to some embodiments of the present disclosure.

DETAILED DESCRIPTION

Figure 1:
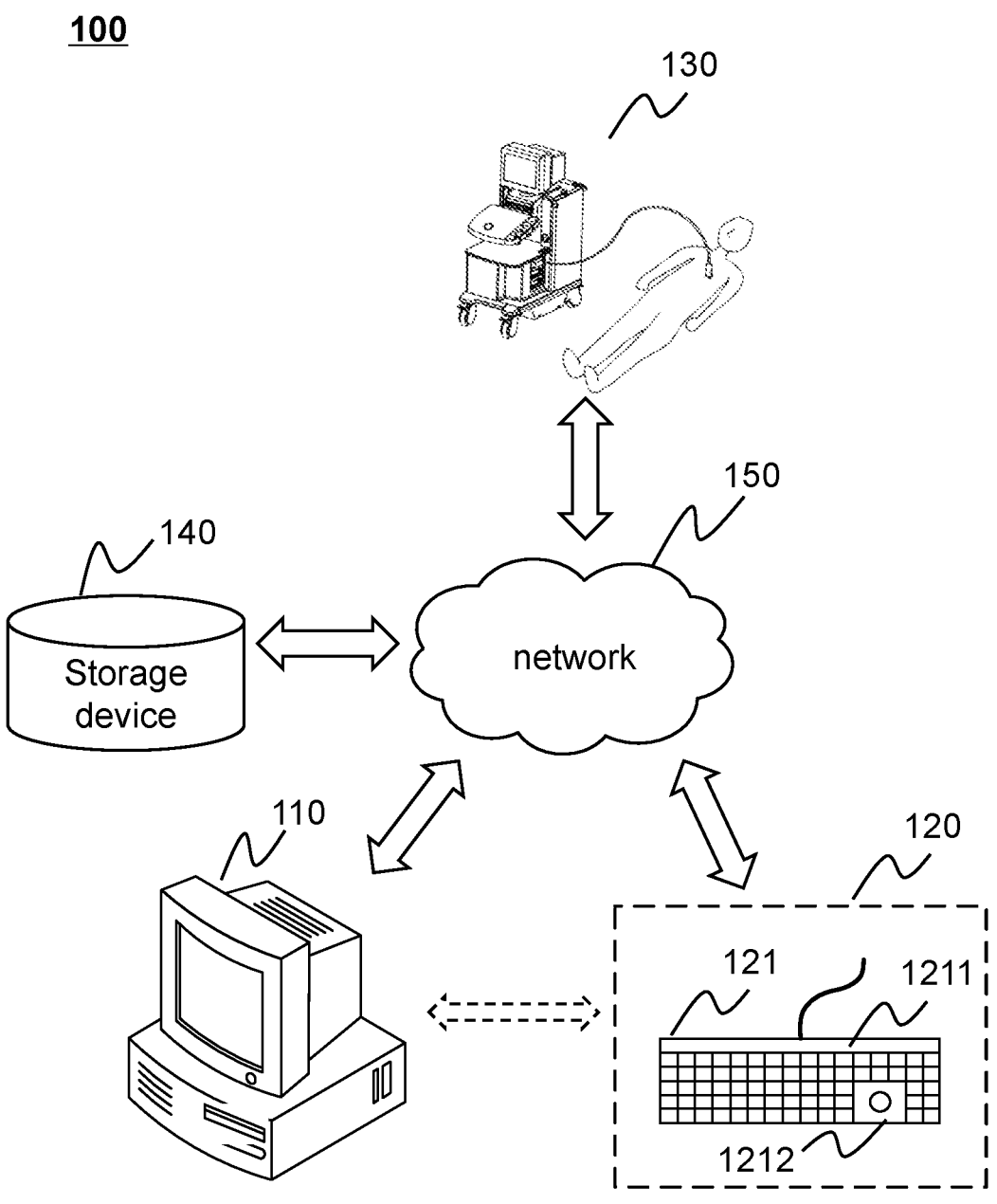
FIG. 1 is a schematic diagram illustrating an application scenario of an ultrasound imaging system according to some embodiments of the present disclosure.

To illustrate the technical solutions of the embodiments of the present disclosure more clearly, the following briefly introduces the drawings that need to be used in the description of the embodiments. Obviously, the accompanying drawings in the following description are only some examples or embodiments of the present disclosure, and those skilled in the art may further apply the present disclosure to other similar scenarios. Unless otherwise apparent from the context or otherwise indicated, the same numeral in the drawings refers to the same structure or operation.

It should be understood that "system", "device", "unit" and/or "module" used herein are used to distinguish different assemblies, elements, assemblies of different levels. However, the words may be replaced by other expressions if other words can achieve the same purpose.

As indicated in the present disclosure and in the claims, unless the context clearly suggests an exception, the words "one," "a," "a kind of," and/or "the" do not specifically refer to the singular but may include the plural. In general, the terms "including" and "comprising" suggest only the inclusion of clearly identified operations and elements, which do not constitute an exclusive list, and the method or device may also include other operations or elements.

Flowcharts are used in the present disclosure to illustrate operations performed by a system according to embodiments of the present disclosure. It should be understood that the preceding or following operations are not necessarily performed in an exact sequence. Instead, the operations may be processed in reverse order or simultaneously. It is also possible to add other operations to these processes, or to remove an operation or operations from them.

FIG. 1 is a schematic diagram illustrating an application scenario of an imaging system according to some embodiments of the present disclosure. An imaging system 100 will hereinafter be referred to as a system 100.

As shown in FIG. 1, in some embodiments, the system 100 may include a processing device 110, a terminal device 120, an imaging device 130, a storage device 140, and a network 150.

The processing device 110 may process data and/or information. The data and/or information may be obtained from the imaging device 130, the terminal device 120, and/or the storage device 140. In some embodiments, the processing device 110 may be a single server or a server group. The server group may be centralized or distributed. In some embodiments, the processing device 110 may be local or remote. For example, the processing device 110 may access information and/or data stored in the imaging device 130, the terminal device 120, and/or the storage device 140 via the network 150. As another example, the processing device 110 may be directly connected to the imaging device 130, the terminal device 120, and/or the storage device 140 to access stored information and/or data. In some embodiments, the processing device 110 may be implemented on a cloud platform. For example, a cloud platform may include a private cloud, a public cloud, a hybrid cloud, a community cloud, a distributed cloud, an inter-cloud, a multi-cloud, etc., or any combination thereof. In some embodiments, the processing device 110 may be implemented by a computing device having one or more components.

In some embodiments, the processing device 110 may control an operation of the imaging device 130. In some embodiments, the processing device 110 may receive an operation instruction sent by a user (e.g., a doctor) via the operation end 120, and based on the operation instruction, the imaging device 130 may be controlled to perform an operation corresponding to the operation instruction, such as, moving a scanning position, performing a scan, etc.

In some embodiments, the processing device 110 may perform a feedback process for a navigation operation as described in some embodiments of the present disclosure. For example, the processing device 110 may obtain a navigation operation instruction sent by the terminal device 120, generate a navigation feedback instruction based on navigation information in the navigation operation instruction and a content displayed on a display screen. The processing device 110 may send the navigation feedback instruction to the terminal device 120 to instruct the terminal device 120 to perform a corresponding operation based on the navigation feedback instruction. The navigation information may be used to indicate a movement of a navigation cursor on the display screen.

In some embodiments, the processing device 110 may include one or more processing engines (e.g., a single-core processing engine or a multi-core multi-chip processing engine). Merely by way of example, the processing device 110 may include a central processing unit (CPU), an application-specific integrated circuit (ASIC), an application-specific instruction processor (ASIP), a graphics processing unit (GPU), a digital signal processor (DSP), a field programmable gate array (FPGA), a reduced instruction set computer (RISC), etc., or any combination of the above.

The terminal device 120 may be configured to facilitate a communication between the user and other components (e.g., the processing device 110, the imaging device 130, etc.) of the system 100. The terminal device 120 may input/output signals, data, information, etc. In some embodiments, the terminal device 120 may enable a user interaction with the processing device 110. For example, the terminal device 120 may display an image of a subject on a display screen. As another example, the terminal device 120 may obtain user's input information through an input device (e.g., a keyboard, a touch screen, a brain wave monitoring device), and transmit the input information to the processing device 110 for further processing. The terminal device 120 may include a mobile device, a tablet computer, a laptop computer etc., or any combination thereof. In some embodiments, the terminal device 120 may be part of the processing device 110. In some embodiments, the terminal device 120 may be integrated with the processing device 110 as an operation station of the imaging device 130. Merely by way of example, the user/operator (for example, a doctor) of the system may control an operation of the imaging device 130 through the operation station.

In some embodiments, the terminal device 120 may include an input control device 121 (also referred to as an input device, e.g., a mouse, a microphone, an imaging sensor, a trackball, a joystick, etc.) and an output device (e.g., a display screen, a speaker, etc.). The input device may input data into the terminal device 120. In some embodiments, the input device 121 may include a navigation operation device (also referred to as a pointing device). The navigation operation device may be configured to perform a navigation operation on the display screen of the terminal device 120.

The input control device 121 may include a body 1211 and a navigation operation component 1212 embedded in the body 1211. The input control device 121 may be configured to convert an input operation of the user into the operation instruction (e.g., a navigation operation instruction, etc.) to be sent to the processing device 110. In some embodiments, the navigation operation component 1212 may generate the navigation operation instruction based on the operation instruction or the input operation of the user. In some embodiments, the navigation operation component 1212 may provide feedback (e.g., vibration feedback, sound feedback, image feedback, etc.) to the user operation based on a feedback instruction (e.g., a navigation feedback instruction), etc., generated and sent by the processing device 110. In some embodiments, the input control device 121 may include a feedback assembly. In some embodiments, the feedback assembly may be configured to provide feedback (e.g., vibration feedback, sound feedback, image feedback, etc.) to the user operation based on a feedback instruction (e.g., a navigation feedback instruction), etc., generated and sent by the processing device 110. In some embodiments, the feedback assembly may be configured to drive the navigation operation component 1212 to provide feedback (e.g., the vibration feedback, the sound feedback, the image feedback, etc.) to the user operation based on a feedback instruction (e.g., a navigation feedback instruction), etc.

In some embodiments, the body 1211 may include a support component configured to provide support for one or more components (e.g., the navigation operation component 1212) of the input control device 121. The support component may include a base. In some embodiments, the body 1211 may be in form of one of a keyboard, a touch screen, a visual reality (VR) device, etc., or any combination thereof. As shown in FIG. 1, in some embodiments, the navigation operation device 1211 may be embedded in the body 1211 of the input control device 121, and may form an integrated structure with the input control device 121. In some embodiments, the input control device 121 and the navigation operation device 1212 may be independently disposed and may respectively communicate with the processing device 110.

In some embodiments, the processing device 110 may be integrated into the input control device 121. In some embodiments, the processing device 110 may be integrated into the imaging device 130.

The imaging device 130 may be configured for imaging of a subject. In some embodiments, the subject may include a biological subject (e.g., a patient) or a non-biological subject (e.g., a phantom). For example, the subject may include a specific part, organ, and/or tissue of a patient. As another example, the subject may include the head, the brain, the neck, the breast, the heart, the lung, the stomach, blood vessels, soft tissues, etc., or any combination thereof. The term "object" or "subject" are used interchangeably in the present disclosure.

In some embodiments, the imaging device 130 may perform a corresponding operation based on the instruction sent from the processing device 110, such as, moving a scan table, performing a scan, etc. In some embodiments, the imaging device 130 may include a single-modality scanner, such as an ultrasound imaging device, a computed tomography (CT) scanner, a magnetic resonance imaging (MRI) scanner, a positron emission tomography (PET) scanner, etc. In some embodiments, the imaging device 130 may include a multi-modality scanner, such as an MR-CT scanner, a CT-PET scanner, etc.

The storage devices 140 stores data or information generated by other devices. In some embodiments, the storage device 140 may store data and/or information collected by the imaging device 130, for example, scan data, etc. In some embodiments, the storage device 130 may store data and/or information generated by the processing device 110 and/or the terminal device 120, such as the navigation operation instruction, the navigation feedback instruction, etc. In some embodiments, the storage device 130 may include one or more storage components, and each component may be an independent device or may be a portion of another device.

In some embodiments, the storage device 140 may store data and/or instructions executed or used by the processing device 110 to perform exemplary methods described in the present disclosure. In some embodiments, the storage device 140 may include a mass storage device, a removable storage device, a volatile read-write memory, a read-only memory (ROM), etc., or any combination thereof. In some embodiments, the storage device 140 may be implemented by the cloud platform described in the present disclosure. For example, a cloud platform may include a private cloud, a public cloud, a hybrid cloud, a community cloud, a distributed cloud, an inter-cloud, a multi-cloud, etc., or any combination thereof.

In some embodiments, the storage device 140 may be connected to the network 150 to communicate with one or more components (e.g., the processing device 110, the terminal device 120, etc.) of the imaging system. The one or more components of the imaging system may access the data or instructions in the storage device 140 via the network 150. In some embodiments, the storage device 140 may be a part of the processing device 110 or may be independent and directly or indirectly connected to the processing device 110.

The network 150 may connect components of the system and/or connect the system to external resource portions. The network 150 may enable communications between the components, and the communications with other portions outside the system, thereby facilitating an exchange of data and/or information. In some embodiments, one or more components of the system 100 (e.g., the processing device 110, the terminal device 120, the imaging device 130, and the storage device 140) may send data and/or information to other components via the network 150. In some embodiments, the network 150 may be any one or more of a wired network or a wireless network. In some embodiments, some, or all of the components of the system 100 may be integrated into a single device, e.g., the processing device 110, the terminal device 120, the imaging device 130, and the storage device 140 may be combined into a single ultrasound imaging device by means of a direct connection such as a cable connection, etc.

It should be noted that the above description is provided for illustrative purposes only and is not intended to limit the scope of the present disclosure. For those skilled in the art, a variety of variations and modifications may be made under the guidance of the contents of the present disclosure. The features, structures, modes, and other characteristics of the exemplary embodiments described herein may be combined in various ways to obtain additional and/or alternative exemplary embodiments. For example, the storage device 140 may be based on a cloud platform, e.g., a public cloud, a private cloud, a community, and hybrid cloud, etc. However, these changes and modifications may not depart from the scope of the present disclosure.

Figure 2:
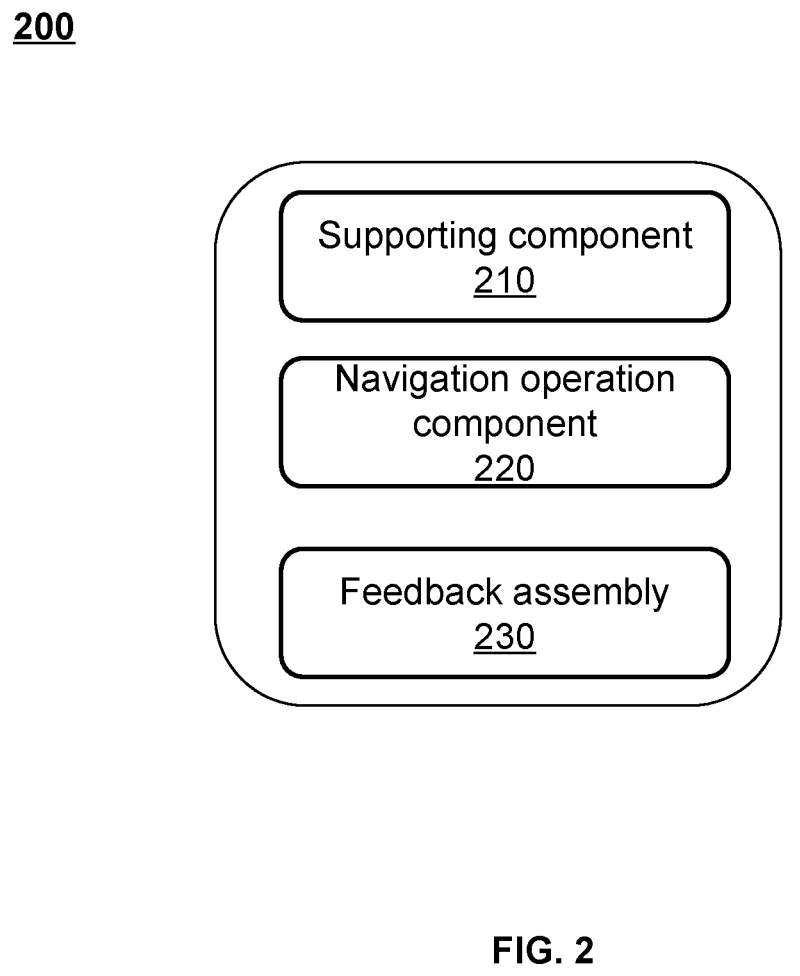

FIG. 2 is a schematic diagram illustrating an exemplary control device for an ultrasound imaging system according to some embodiments of the present disclosure.

As shown in FIG. 2, in some embodiments, a control device 200 (also referred to as a navigation operation device) may include a supporting component 210, a navigation operation component 220, and a feedback assembly 230. In some embodiments, the device 200 may be implemented on the terminal device 120. In some embodiments, the device 200 may include the processing device 110 and a portion of the terminal device 120 (e.g., an input device) as described in FIG. 1.

In some embodiments, the navigation operation component 220 may be configured to perform a navigation operation on a display screen (e.g., the display screen of the processing device 110) of an imaging system (e.g., the ultrasound imaging system (e.g., the system 100)). As used herein, a navigation operation refers to guiding an element (e.g., a cursor) to perform an action on a display screen according to an input (or an input operation) of the navigation operation device. In other words, an input (or input operation) of the navigation operation device may be converted into the action of the element (e.g., a cursor) on the display screen, and the conversion process may be referred to as a navigation operation. The input operation of the navigation operation device may include dragging a component of the navigation operation device, clicking a component of the navigation device, rotating a component of the navigation operation device, pressing a component of the navigation operation device, lifting a component of the navigation operation device, etc. The action of the element (e.g., a cursor) on the display screen may include moving the element (e.g., a cursor), stopping the movement of the element (e.g., a cursor), etc. The action of the element may be processed by a processing device and determine a corresponding result, such as a confirmation, selection, copying, deleting, etc.

For example, the navigation operation may include rotating a trackball of the navigation operation device and the rotation of the trackball of the navigation operation device may be converted into the moving of a cursor. As another example, the navigation operation may include clicking a trackball of the navigation operation device and the clicking of the trackball of the navigation operation device may be converted into the stopping of the cursor, and the stopping of the cursor may be converted into the selection of a target object (e.g., a region of interest) where the cursor is located.

The supporting component 210 may provide a support for one or more components of the navigation operation device 200. In some embodiments, the support may include a base or a substrate. The one or more components of the navigation operation device 200 may be provided on the base or a substrate. For example, the navigation operation component 220 may be arranged on the base or a substrate. In some embodiments, the supporting component 210 may include a house. At least a portion of the navigation operation component 220 may be inserted within the house.

The navigation operation component 220 may facilitate a communication of a user with the navigation operation device. The user may generate the user operation via the navigation operation component. The navigation operation component 220 may include a trackball, a mouse, a joystick, a touch screen, a graphics tablet, etc.

The feedback assembly 230 may be configured to drive, based on the navigation operation of the navigation operation component 220, the navigation operation component 220 and/or an element of the feedback assembly 230 to provide feedback on the navigation operation.

In some embodiments, the navigation operation of the navigation operation component 220 may be determined based on an input of a user via the navigation operation component 220. The feedback assembly 230 driving, based on the navigation operation of the navigation operation component 220, the navigation operation component 220 and/or an element of the feedback assembly 230 to provide feedback on the navigation operation may include driving, based on an input operation of a user via the navigation operation component 220, the navigation operation component 220 and/or an element of the feedback assembly 230 to provide feedback on the input operation.

In some embodiments, the navigation operation may correspond to an operation state of the navigation operation component. For example, the operation state may include standing still, moving, vibrating, rotating, etc. The feedback assembly driving, based on the navigation operation of the navigation operation component 220, the navigation operation component 220 and/or an element of the feedback assembly 230 to provide feedback on the navigation operation may include driving, based on the operation state of the navigation operation component, the navigation operation component and/or the element of the feedback assembly to provide the feedback on the navigation operation In some embodiments, the feedback on the navigation operation may include different types, e.g., vibration feedback, movement feedback, force feedback, sound feedback, image feedback, video feedback, etc.

The force feedback may include resistance feedback, assistance feedback, an elastic feedback, etc. The resistance feedback refers to providing a resistance force having a direction that is opposite to an original force applied to the navigation operation component by a user for performing a navigation operation; the assistance feedback refers to providing an assistance force having a direction that is the same as an original force applied to the navigation operation component by a user for performing a navigation operation. For example, the force feedback on the navigation operation may include providing a resistance force or an assistance force to the navigation operation to adjust a force received by the user when the user performs an input operation via the navigation operation component. Specifically, when the user performs a navigation operation through the navigation operation component, a certain resistance force may be generated and received by the user due to friction between the components of the navigation operation device, etc. When the feedback on the navigation operation is required, a torque in an opposite direction of the original force may be applied through the feedback assembly (e.g., a motor, etc.) to provide the user with an additional resistance force; or a torque in the same direction of the original force may be applied through the feedback assembly (e.g., a motor, etc.) to provide the user with an additional assistance force to reduce the friction when moving the navigation operation component. The applied torque may include a constant torque or a variable torque. In some embodiments, different users may dynamically adjust the resistance of the navigation operation to meet the individual needs of different users through the resistance force and/or assistance force (i.e., torque) provided to the navigation operation.

In some embodiments, as the device ages and a mechanical structure ages, the resistance when the navigation operation component is operated may increase, and an assistance force may be provided to the navigation operation so that the user always maintains a good feel when operating the navigation operation component.

In some embodiments, the assistance force provided to the navigation operation component may be equal to the original resistance assistance force applied to the navigation operation component for performing the navigation operation, allowing for a zero resistance operation by the user.

The elastic feedback refers to providing an elastic force to a user when performing a navigation operation. In some embodiments, when the navigation operation device performs the navigation operation for moving an element (e.g., a cursor) from a point to another point on the display screen, a constant torque may be applied through the component of the feedback assembly, while a magnitude of the torque may increase linearly with a magnitude of a displacement of the navigation operation component, thereby implementing a simulation of the elastic force. The constant torque may have a direction opposite to the original force by a user applied to the navigation operation component for performing the navigation operation.

For the vibration feedback, the navigation operation component 220 may be controlled by the feedback assembly to make a high-frequency reciprocating motion to achieve a vibration effect.

In some embodiments, the navigation operation component 220 may be controlled by the feedback assembly to move or rotate with a specified speed to achieve the movement feedback. In some embodiments, the navigation operation component 220 may arrive at a specified position at the specified speed.

In some embodiments, different types of feedback may be determined by the system automatically or by a user manually according to actual requirements. The feedback assembly 230 may drive, based on the navigation operation of the navigation operation component 220, the navigation operation component 220 and/or an element of the feedback assembly 230 to provide feedback on the navigation operation according to one type of the feedback. For example, the system may determine that if the navigation operation includes moving the element from one point to another point, and the element is within a region of interest on the display screen, the system may determine that the feedback may include the vibration feedback; if the navigation operation includes moving the element from one point to another point, and the element is keep away from a region of interest on the display screen, the system may determine that the feedback may include a force feedback. As another example, the user may set the force feedback according to the user preference. If the user prefers a larger resistance for operating the navigation operation component, the user may set such that an additional resistance force may applied to the navigation operation component when the user operates the navigation operation component; if the user prefers no resistance for operating the navigation operation component, the user may set such that an additional assistance force may applied to the navigation operation component when the user operates the navigation operation component.

In some embodiments, the feedback assembly 230 may include a driving component, and the driving component may be configured to drive the navigation operation component 220 to provide feedback based on the navigation operation.

Figure 3A:
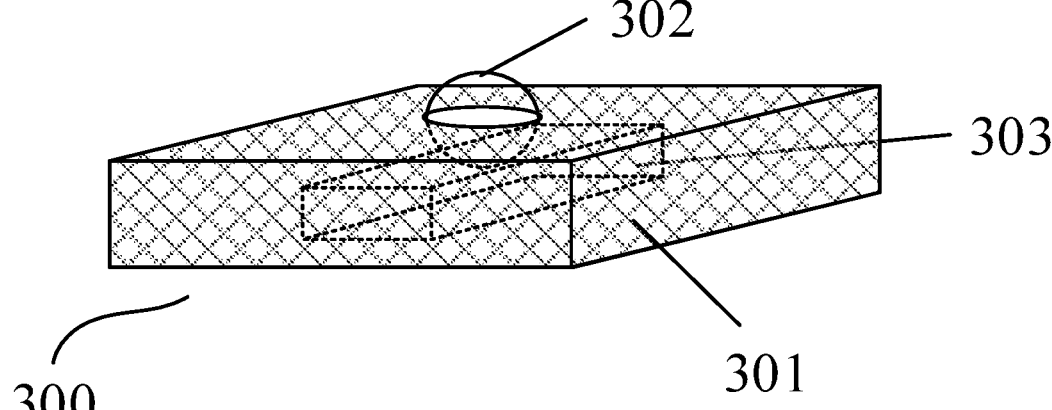
FIG. 3A and FIG. 3B are schematic diagrams illustrating an exemplary navigation operation device according to some embodiments of the present disclosure.
Figure 3B:
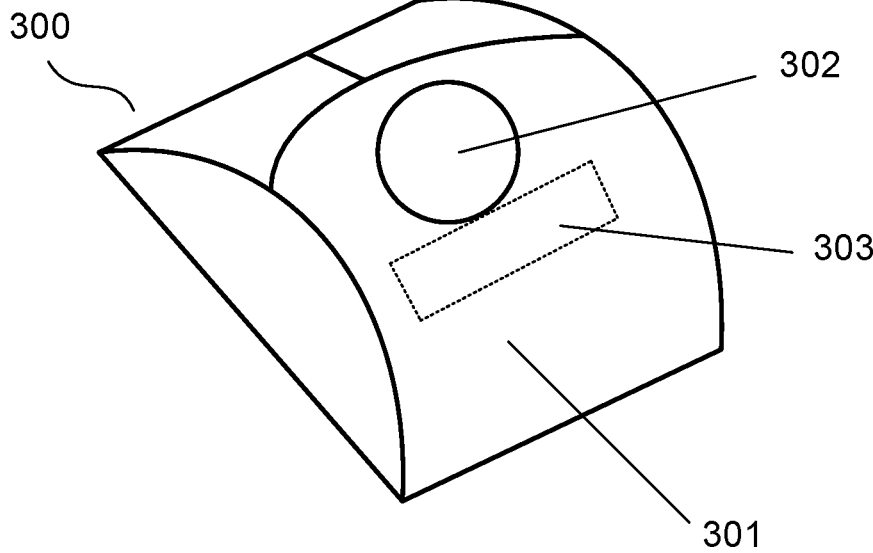
Figure 3C:
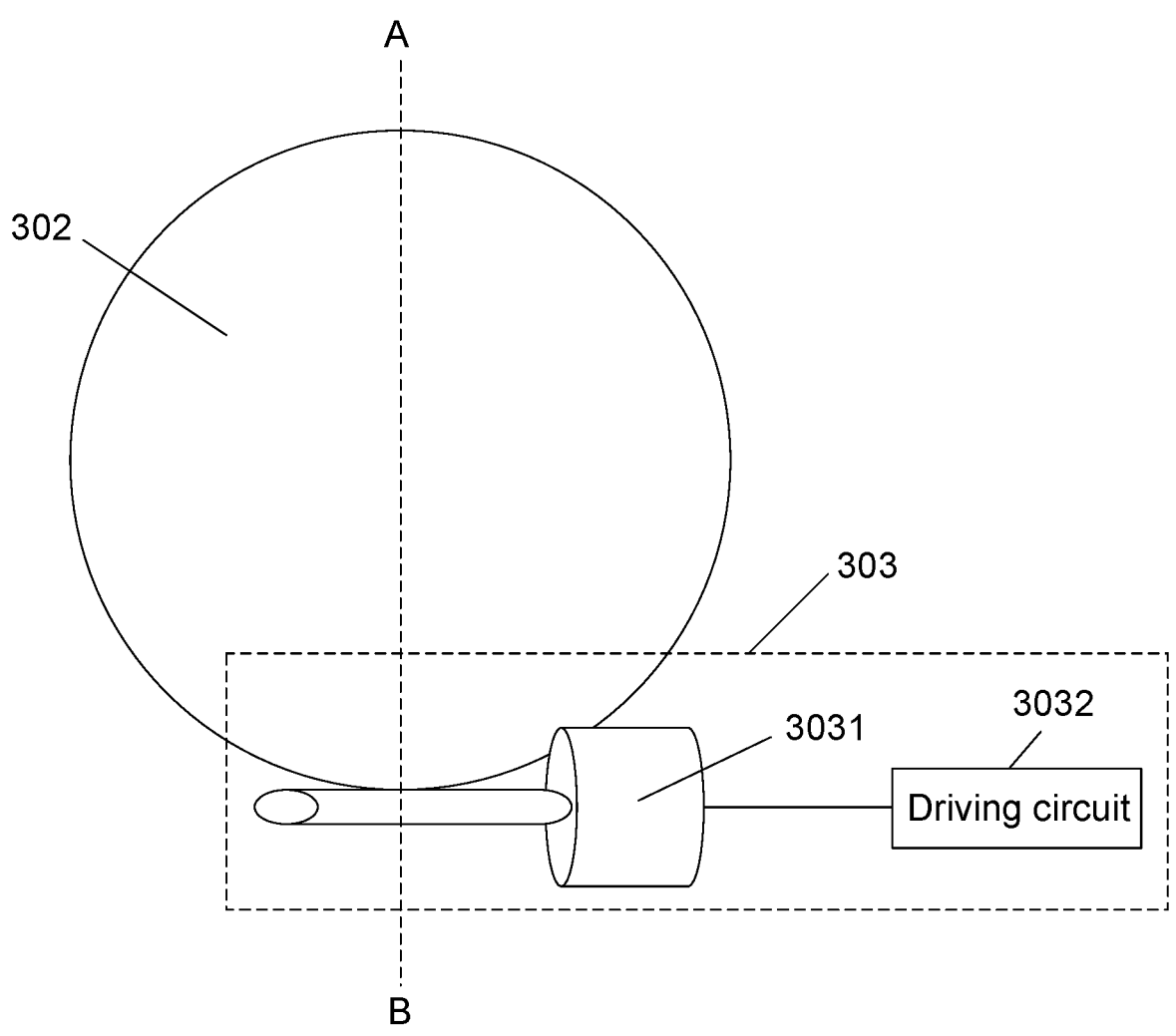
FIG. 3C is a schematic diagram illustrating a connection between a navigation operation component and a driving component according to some embodiments of the present disclosure.

In some embodiments, the driving component may include at least two motors (e.g., motors 3031-1 and 3031-2 in FIG. 3F) and a driving circuit (e.g., driving circuit 3032 in FIG. 3C). Each of the motors may include a rotating shaft, and the driving circuit may be configured to drive the motor to rotate around the rotating shaft. The rotating shaft may be connected with the navigation operation component 220. More descriptions for the driving component may be found elsewhere in the present disclosure.

In some embodiments, the driving component may include other devices capable of providing power, such as an internal combustion engine, a mechanical driving component (such as springs, etc.), a bioenergy driving component, etc.

In some embodiments, the feedback assembly 230 may include a controller. The controller may be configured to control the feedback assembly 230 and/or the navigation operation component 220 to provide feedback. For example, the feedback generation module 720 may control the feedback assembly and/or the navigation operation component 220 to provide feedback according to process 500. More descriptions for the navigation operation device may be found elsewhere in the present disclose (e.g., FIGS. 3A-3G and FIG. 4, and the descriptions thereof).

In some embodiments, the control device for the ultrasound imaging system may include a mouse, etc., for example, a photoelectric mouse, a laser mouse, a mechanical mouse, etc.

FIGS. 3A and 3B are schematic diagrams illustrating an exemplary navigation operation device according to some embodiments of the present disclosure.

As shown in FIGS. 3A and 3B, a navigation operation device 300 may include a supporting component 301, a navigation operation component 302, and a driving component 303. In some embodiments, the device 300 may be an exemplary embodiment of the device 200.

In some embodiments, the navigation operation component 302 as well as the driving component 303 may both be installed on the supporting component 301. In some embodiments, the navigation operation component 302 may move driven by the driving component 303 to perform a navigation operation on a display screen (e.g., the display screen of the terminal device 120) of an imaging system (e.g., an ultrasound imaging system).

In some embodiments, the supporting component 301 may include a hollow structure. For example, the supporting component 301 may include a housing, and at least a portion of the navigation operation component 302 may be embedded in the housing. Under an action of an external force, the navigation operation component 302 may rotate freely and maintain a constant position relative to the supporting component 301. In some embodiments, at least portion of the driving component 103 may be disposed within the supporting component 301.

In some embodiments, the housing of the supporting component 101 in contact with an operator's hand may be an arc protruding outward, to adapt to a bending of the operator's hand to improve operation comfort.

In some embodiments, as shown in FIG. 3B, the housing of the supporting component 301 may include one or more buttons. The one or more buttons may be configured for input operations for a user, for example, a selection operation, a confirmation operation, etc. For example, the one or more buttons may include a left button and a right button distributed on the left and right to enable associated operations.

In some embodiments, the navigation operation component 302 may include a trackball, etc., which is capable of detecting changes in position, as well as indicating operations such as cursor movement and selection. This present disclosure will hereinafter be described using the example of the navigation operation component 302 as a trackball.

In some embodiments, the driving component 303 may provide power for the operation of the navigation operation component 302. For example, the driving component 303 may drive the navigation operation component 302 to rotate. Accordingly, a rotation of the navigation operation component 302 may not be limited to be driven by a human touch, thereby enriching a control mode of the device 300. The navigation operation device may realize a navigation feedback, a non-contact navigation, and other functions while implementing a basic function of the navigation operation, thereby improving a diversity of the functions of the navigation operation device, and implementing a broader application of the navigation operation device.

In some embodiments, the driving component 303 may drive the navigation operation component 302 to provide feedback for the navigation operation. The feedback for the navigation operation may include vibration feedback, movement feedback, force feedback, sound feedback, image feedback, video feedback, etc. For example, the driving component 303 may drive the navigation operation component 302 to rotate to give feedback on the movement of the cursor on the screen, and may also adjust a rotation speed of the navigation operation component 302 according to a moving speed of the cursor. For another example, the driving component 303 may drive the navigation operation component 302 to vibrate to implement the force feedback for operations such as a cursor clicking. Frequency and amplitude of the vibration may be determined according to the properties of the object clicked by the cursor.

To enable control of the rotation of the navigation operation component 302 by the driving component 303, in some embodiments, the driving component 303 may include a motor and a driving circuit. The motor may include a rotating shaft. The rotating shaft may be disposed in contact with the navigation operation component. The driving circuit may be connected with the motor, and the driving circuit may be configured to drive the motor to rotate. The driving circuit may be connected with a controller (e.g., a processing device). The controller may control the motor to rotate via the driving circuit. As shown in FIG. 3C, in some embodiments, the driving component 303 may include a motor 3031 and a driving circuit 3032. The rotating shaft of the motor 3031 may be disposed in contact with the navigation operation component 302, the driving circuit 3032 may be connected with the motor 3031, and the driving circuit 3032 may be configured to drive the motor 3031 to rotate. The rotation of the motor 3031 may cause a rotation of the rotating shaft. The rotation of the rotating shaft of the motor 3031 may cause a rotation of the navigation operation component 302.

In some embodiments, the motor 3031 may include an in-laid motor embedded within the navigation operation component 302. The motor 3031 may rotate and drive the navigation operation component 302 to rotate when powered on. In some embodiments, when the navigation operation component 302 is made of a magnetic material, the driving component 303 may include an electromagnetic device disposed around the navigation operation component 302. The electromagnetic device may generate a magnetic force acting on the navigation operation component 302 when powered on, and the navigation operation component 302 may rotate under the magnetic force.

In some embodiments, the driving component 303 may include a vibration motor in contact with the navigation operation component 302. The vibration motor may vibrate and drive the navigation operation component 302 to vibrate when powered on.

As shown in FIG. 3C, in some embodiments, the rotating shaft of the motor 3031 may be disposed axially tangential to the navigation operation component 302, so that when the motor 3031 rotates, the navigation operation component 302 may be driven to rotate utilizing a friction on a contact surface between the rotating shaft of the motor 3031 and the navigation operation component 302. In some embodiments, the motor 3031 may include any type of motor such as a brushless motor, a brush motor, a servo motor, or any combination thereof, and the driving circuit 3032 corresponding to the motor may be determined based on the specific type of the motor 303.

In some embodiments, the driving circuit 3032 in the driving component 303 may be configured to convert an electrical energy to a mechanical energy and drive the motor 3031 to rotate through the mechanical energy obtained from the conversion, thereby rotating the shaft of the motor 3031. As the rotating shaft of the motor 3031 is axially tangent to the navigation operation component 302, when the rotating shaft of the motor 3031 rotates, the friction force with the same direction as the direction of rotation of the rotating shaft may be generated on the contact surface between the rotating shaft and the navigation operation component 302, and under the action of the friction force, the navigation operation component 302 may rotate.

Figure 3D:
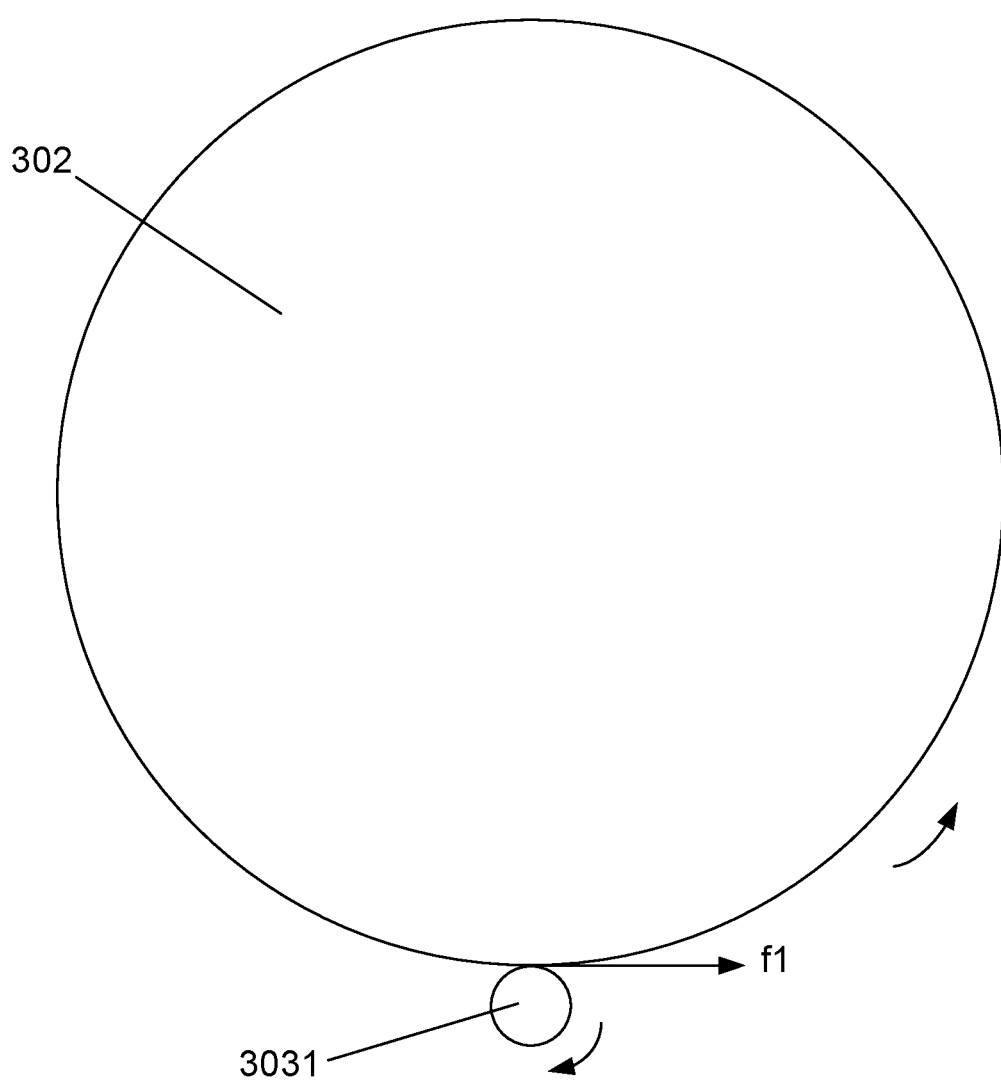
FIG. 3D and FIG. 3E are schematic diagrams illustrating a section force between a rotating shaft on a motor and a navigation operation component according to some embodiments of the present disclosure.
Figure 3E:
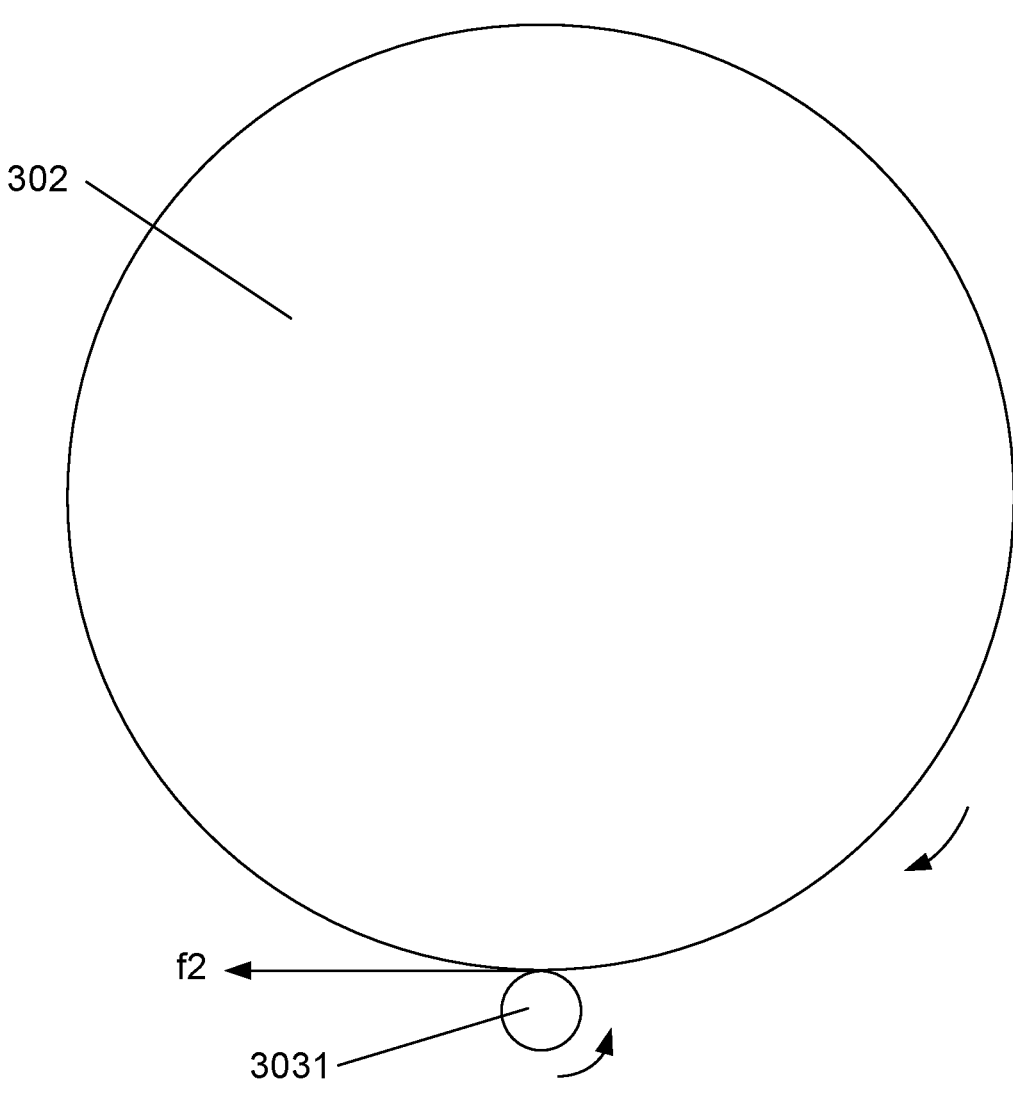

FIGS. 3D and 3E are schematic diagrams illustrating a section force between the rotating shaft of the motor 3031 and the navigation operation component 302 obtained by taking a dashed line in FIG. 3C as a section. An axial direction of the rotating shaft of the motor 3031 may be the direction perpendicular to the section of the navigation operation component 302 in FIGS. 3D and 3E. As shown in FIG. 3D, when the rotating shaft of the motor 3031 rotates in a clockwise direction, a friction force f1 may be generated at a contact surface between the rotating shaft and the navigation operation component 302, and the friction force f1 may drive the entire navigation operation component 302 to rotate in a counterclockwise direction. As shown in FIG. 3E, when the rotating shaft of the motor 3031 rotates in the counterclockwise direction, a friction force f2 may be generated at the contact surface between the rotating shaft and the navigation operation component 302, and the action of the friction force f2 may drive the entire navigation operation component 302 to rotate in the clockwise direction.

In some embodiments of the present disclosure, the rotating shaft of the motor may be disposed in contact with the navigation operation component (e.g., a trackball), and in a case where a driving circuit drives the motor to rotate, the navigation operation component may be driven to rotate relying on the friction generated on the contact surface between the rotating shaft and the navigation operation component, so as to realize an active control by the driving component of the movement of the navigation operation component, and thus to improve a function diversity and a wide application of the navigation operation device.

To control the navigation operation component 302 to move in a plurality of directions (e.g., rotate, translate, etc.), in some embodiments, the driving component 303 may include a plurality of motors, e.g., 2, 3, 6, etc. In some embodiments, these motors may enable a full range of positional movement in a two-dimensional (2D) plane or in a three-dimensional (3D) space through the navigation operation component 302. For example, at least two motors may be used to implement the movement in x-axis and y-axis directions in the 2D plane to feedback 2D positional changes on a planar display device. As another example, at least three motors may be used to realize the movement in the x-axis, y-axis, and z-axis directions in the 3D space to feedback 3D position changes on a 3D display device such as a VR device. In some embodiments, each motor in the driving component 303 may correspond to a driving circuit, i.e., with M (M>1) motors, there may be M matched driving circuits. In some embodiments, a number of driving circuits may be less than a number of motors, i.e., at least a portion of the motors (more than 1) in the driving component 303 may be driven by a single driving circuit. In some embodiments, these motors may be disposed in a plurality of different positions, thereby driving the navigation operation component 302 in different directions.

Figure 3F:
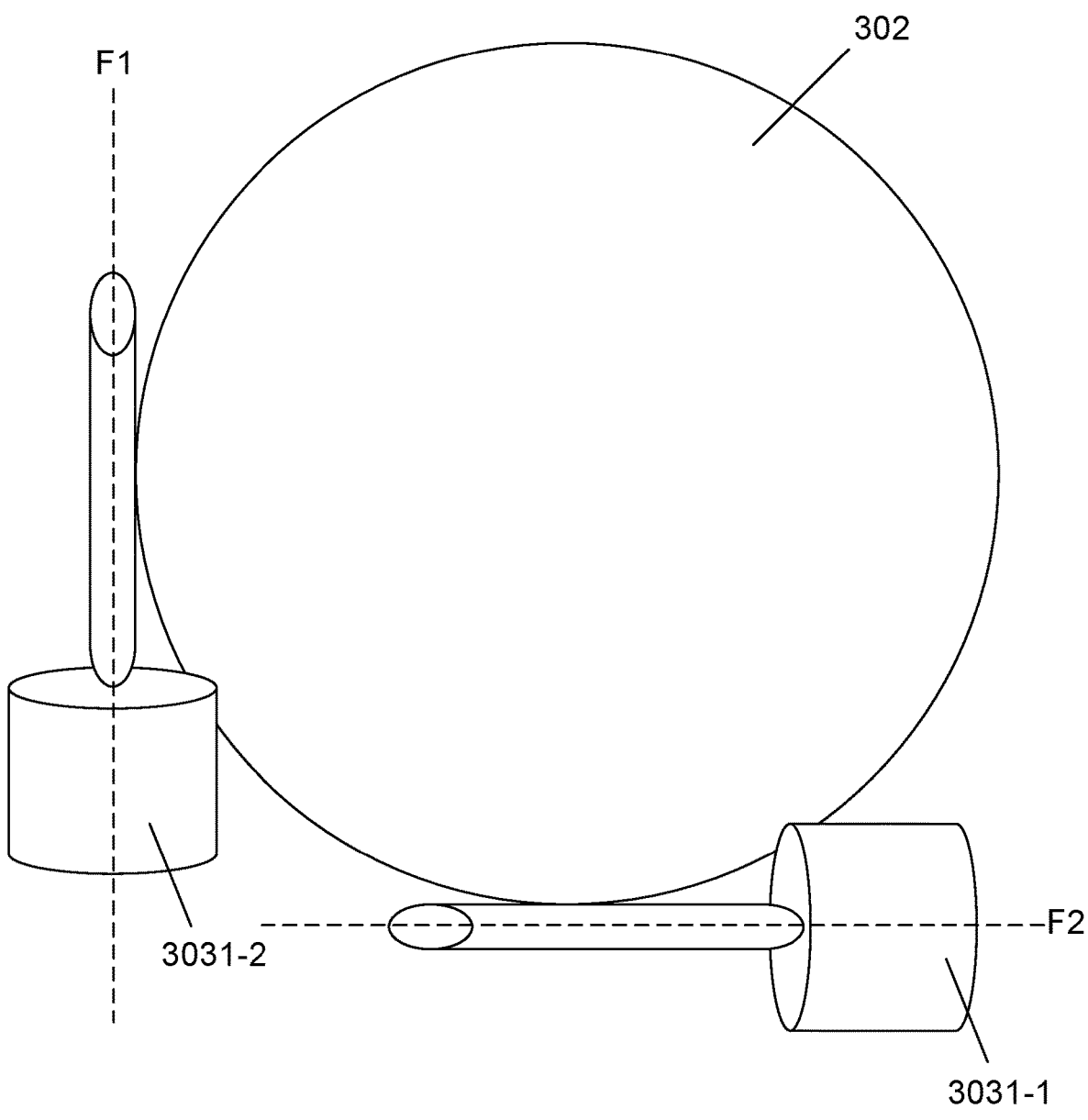
FIG. 3F is a schematic diagram illustrating a connection between a navigation operation component and a motor according to some embodiments of the present disclosure.

For example, as shown in FIG. 3F, a first motor 3031-1 and a second motor 3031-2 may be included in the driving component 103, and the first motor 3031-1 and the second motor 3031-2 may be disposed at different positions of the navigation operation component 302. The rotating shaft of the first motor 3031-1 may be provided in contact with the navigation operation component 302 along a first direction F1, and the rotating shaft of the second motor 3031-2 may be disposed in contact with the navigation operation component 302 along a second direction F2. The first direction F1 and the second direction F2 may be different directions. In some embodiments, the first direction F1 may be perpendicular to the second direction F2.

In some embodiments, the first direction F1 may be a direction in which the rotating shaft of the first motor 3031-1 extends, and the second direction F2 may be a direction in which the rotating shaft of the second motor 3031-2 extends. Under an action of the first motor 3031-1, the navigation operation component 302 may rotate in a first plane perpendicular to the first direction F1. When the first motor 3031-1 rotates in the clockwise direction, the navigation operation component 302 may perform a counterclockwise rotation in the first plane perpendicular to the first direction F1; when the first motor 3031-1 rotates in the counterclockwise direction, the navigation operation component 302 may perform a clockwise rotation in the first plane perpendicular to the first direction F1. Under the action of the second motor 3031-2, the navigation operation component 302 may then rotate in a second plane perpendicular to the second direction F2. When the second motor 3031-2 rotates in the clockwise direction, the navigation operation component 302 may rotate in the counterclockwise direction in the second plane perpendicular to the second direction F2, and when the second motor 3031-2 rotates in the counterclockwise direction, the navigation operation component 302 may rotate in the clockwise direction in the second plane perpendicular to the second direction F2. In this way, the navigation operation component 302 may be controlled to rotate in the first plane perpendicular to the first direction F1 when the first motor 3031-1 is controlled to rotate, and the navigation operation component 302 may be controlled to rotate in the second plane perpendicular to the second direction F2 when the second motor 3031-2 is controlled to rotate. By respectively controlling the rotation of the motors disposed at different positions, the navigation operation component 302 may be controlled to rotate in different planes (also referred to as directions).

In some embodiments, the first motor 3031-1 and the second motor 3031-2 may be provided vertically in order to simplify the structure of the driving component 303 while allowing the navigation operation component 302 to rotate freely in any direction. As shown in FIG. 3F, the first direction F1 may be perpendicular to the second direction F2.

In some embodiments, the device 300 (e.g., a controller, the processing device 110) may receive control instructions for the first motor 3031-1 and the second motor 3031-2, respectively. The control instructions (e.g., a first navigation feedback instruction, a second navigation feedback instruction, etc., as described in FIG. 5) may be input by a user or determined based on the navigation operation and/or a display content on a display screen. The device 300 (e.g., a controller, the processing device 110) may parse the instructions to obtain target parameters (e.g., a torque, a speed, etc.) for the first motor 3031-1 and the second motor 3031-2, respectively. The device 300 (e.g., the controller, the processing device 110) may determine operation parameters (e.g., a circuit pass, an output voltage, etc.) for the driving circuits associated with the first motor 3031-1 and the second motor 3031-2, respectively, through an algorithm such as a field-oriented control (FOC) algorithm based on the target parameters. The device 300 (e.g., the controller, the processing device 110) may control the first motor 3031-1 and the second motor 3031-2 to rotate according to these operation parameters for the driving circuits associated with the first motor 3031-1 and the second motor 3031-2, respectively. As shown in FIG. 3 F, by respectively controlling the target parameters of the first motor M1 and the target parameters of the second motor M2, the rotation of the navigation operation component 302 in two mutually perpendicular directions may be implemented respectively, so that the navigation operation component 302 may be controlled to rotate in any direction in the 2D plane, thereby ensuring flexibility and an application range of the navigation operation member 302.

In some embodiments, the device 300 may further include a magnetic field sensor disposed on the motor 3031, which may be configured to detect a rotation state of the motor 3031. In some embodiments, the device 300 may determine a rotation track of the navigation operation component 302 based on the rotation state of the motor 3031, thereby determining a position of the cursor on the display screen, so as to feedback to the display screen for displaying and realize the navigation operation. In some embodiments, the magnetic field sensor in the device 300 may include a Hall sensor, etc.

In some embodiments, the device 300 may also include a photoelectric sensor disposed below the navigation operation component 302. The photoelectric sensor may be configured to detect a rotational state of the navigation operation component 302. With the rotation of the navigation operation component 302, a light and shadow of the photoelectric sensor acting on the navigation operation component 302 changes, and based on the light and shadow change, the rotation state of the navigation operation component 302 may be determined. Based on the rotation state, the position of the cursor on the display screen may be determined, so as to realize cursor positioning and navigation.

In some embodiments, the device 300 may determine the rotation state of the navigation operation component 302 in other ways, such as, by any one or more of a variety of sensors such as an infrared sensor, a laser sensor, a mechanical sensor, etc.

Figure 3G:
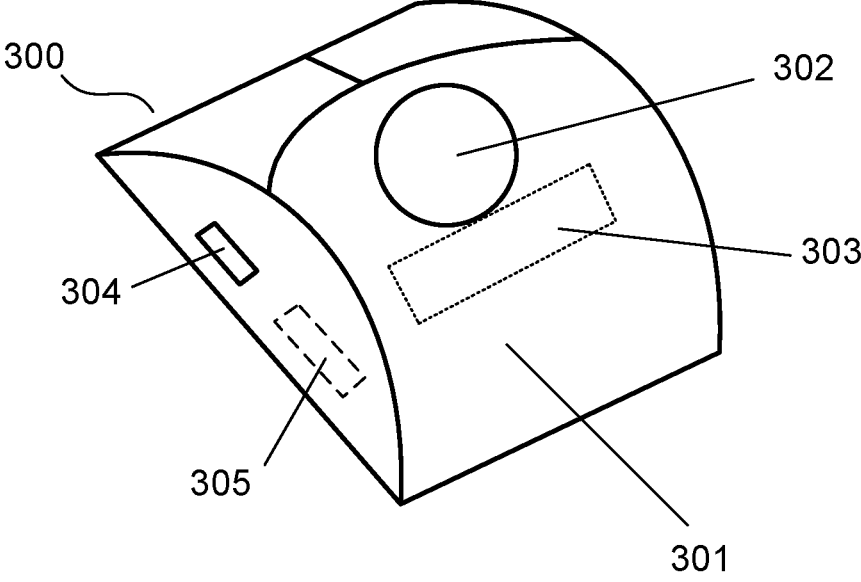
FIG. 3G is a schematic diagram illustrating an exemplary control device for an ultrasound imaging system according to some other embodiments of the present disclosure.

To enable a mutual communication between the device 300 and the imaging device, in some embodiments, the device 300 may include a data transmission interface and/or a wireless communication module for communicating with the imaging device. As shown in FIG. 3G, in some embodiments, the device 300 may include a data transmission interface 304 and a wireless communication module 305. The present disclosure does not limit specific positions of the data transmission interface 304 and the wireless communication module 305, e.g., in FIG. 3G, the data transmission interface 304 is located on a side wall of the supporting component 301, and the wireless communication module 305 is located on the interior of the supporting component 301.

In some embodiments, the data transmission interface 304 may include one or more of wired connections and wireless connections, such as a universal serial bus (USB) interface, an RS232, an RS485, a cable interface, a 4G/5G wireless, a Bluetooth, a WIFI, etc., and may include the interface using a public transmission protocol and/or the interface using a private transmission protocol. The wireless communication module 305 may include any wireless communication modules such as a Bluetooth module, a WIFI module, etc., or any combination thereof.

In some embodiments, the device 300 may communicate with a control device (e.g., the processing device 110) in the ultrasound imaging system (e.g., the system 100) through the data transmission interface and/or the wireless communication module.

Figure 4:
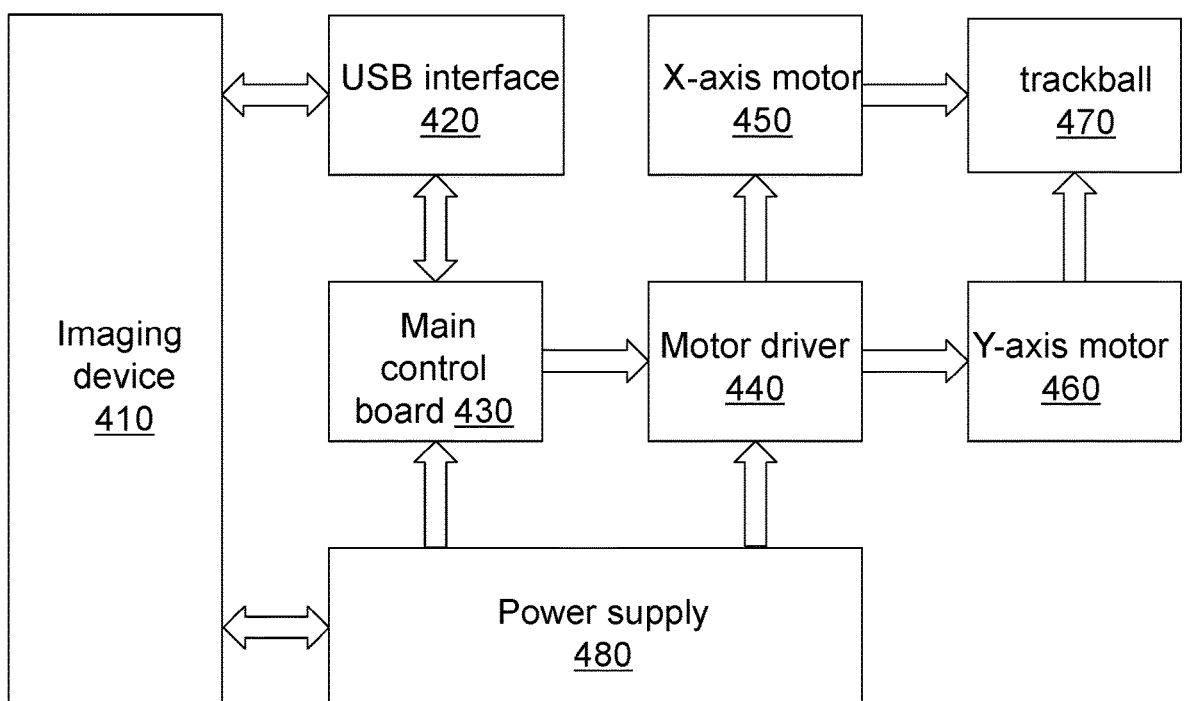
FIG. 4 is a schematic diagram illustrating an exemplary ultrasound imaging system according to some embodiments of the present disclosure.

FIG. 4 is a schematic diagram illustrating an imaging system according to some embodiments of the present disclosure. An imaging system 400 (e.g., an ultrasound imaging system) may be referred to in the present disclosure as the system 400.

As shown in FIG. 4, in some embodiments, the system 400 may include an imaging device 410, a power supply, and a navigation operation device. The navigation operation device may include a main control board 430, a motor driver 440, an X-axis motor 450, a Y-axis motor 460, a trackball 470, and a power supply 480.

The imaging device 410 may be configured to perform a scanning imaging on a target object (e.g., a patient, etc.). In some embodiments, the imaging device 410 may include the imaging device 130. The imaging device 410 may be connected with a USB interface 420 and the power supply 480.

The navigation operation device may include the USB interface 420, the main control board 430, the motor driver 440, the X-axis motor 450, the Y-axis motor 460, and the trackball 470.

As a control core of the navigation operation device, the main control board 430 may be connected with the imaging device 410 through the USB interface 420 and may control operations of the X-axis motor 450 and the Y-axis motor 460 through the motor driver 440 to control a movement of the trackball 470. In some embodiments, the main control board 430 may be implemented using various development boards (e.g., an EPS32, etc.). The main control board 430 may operate an embedded system (e.g., an embedded Linux, etc.), which performs operations such as computing, control, communication, etc.

The USB interface 420 may transmit a control instruction issued by the imaging device 410 to the main control board 430. The control instruction may be analyzed for determining one or more control parameters. The X-axis motor 450 and the Y-axis motor 460 may be controlled to rotate through the motor driver 440 based on the one or more control parameters, thereby driving the trackball 470 to rotate.

The motor driver 440 may be used to drive a rotation shaft of the X-axis motor 450 and/or the Y-axis motor 460 to rotate to control the rotation of the trackball. The motor driver 440 may be connected with the main control board 430, the X-axis motor 450, and the Y-axis motor 460. The X-axis motor 450 and the Y-axis motor 460 may be disposed in contact with the trackball 470. In some embodiments, the motor driver 440 may be equivalent to the driving circuit 3032, the X-axis motor 450 and the Y-axis motor 460 may be equivalent to the first motor 3031-1 and the second motor 3031-2, and the trackball 470 may be equivalent to the navigation operation component 302.

The power supply 480 may be connected with the main control board 430 and the motor driver 440 to power the entire navigation operation device. In some embodiments, the power supply 480 may be an independent battery that powers the main control board 430 and the motor driver 440, or the power supply 480 may be a portion of the imaging device 40 based on a connection to the imaging device 410. In some embodiments, the power supply 480 may include a plurality of sub-power supplies. The main control board 430 and the motor driver 440 may be powered using different sub-power supplies.

FIG. 5 is a flowchart illustrating an exemplary feedback mode for a navigation operation according to some embodiments of the present disclosure.

As shown in FIG. 4, a process 500 may include the following operations. In some embodiments, the process 500 may be performed by the processing device 110 and/or the controller 232. In some embodiments, the feedback mode for the navigation operation shown in the process 500 may be implemented on the device 200.

In 510, a navigation operation instruction sent by the navigation operation component may be obtained. In some embodiments, operation 510 may be performed by an instruction receiving module 710.

The navigation operation instruction refers to the instruction for directing how a navigation cursor in a user interface moves across a display screen (e.g., the display screen in the processing device 110) in an imaging system (e.g., the system 100, the system 400). The navigation operation instruction may indicate a navigation operation. In some embodiments, the navigation operation instruction may include navigation information indicating a movement of the navigation cursor on the display screen of the imaging system. The navigation information may include at least a portion of the information including a position of the navigation cursor, a moving direction, a moving distance, a moving speed, etc. For more contents on the navigation operation component, please refer to relevant descriptions of FIGS. 2 and 3A-3G, which are not repeated here. In some embodiments, a navigation operation device may include a controller, and the controller may receive the navigation operation instruction sent by the navigation operation component 220.

In some embodiments, an imaging device (e.g., the imaging device 130, the imaging device 410) in the imaging system may generate a medical image and display the medical image on the display screen. An operation device (e.g., the terminal device 120) in the imaging system may be configured to perform relative input controls including a cursor movement, an information input, and a page jump, etc. In some embodiments, the user (e.g., a doctor, etc.) may move the navigation cursor on the display screen by operating the navigation operation component (e.g., the navigation operation component 220, the navigation operation component 302) in the navigation operation device (e.g., the device 200, the device 300), and the navigation operation device may generate, based on an input operation of the user, the navigation operation instruction used to indicate the navigation information for the movement of the navigation cursor on the display screen. For example, the input operation of the user may include toggling a trackball in the navigation operation device to move along a first direction, and the navigation operation instruction may instruct the navigation cursor to move along the first direction. The input operation of the user may include toggling the trackball to move a distance s, and the navigation operation instruction may instruct the navigation cursor to move a distance S. The distances s and S may be converted according to a predetermined rule, for example, the distance s may be 1 mm, and the corresponding distance S may be 10 pixel dots on the display screen.

In 520, a navigation feedback instruction may be generated based on the navigation operation instruction (e.g., the navigation information or the navigation operation) and a content displayed on the display screen. In some embodiments, the operation 520 may be performed by a feedback generation module 720.

The navigation feedback instruction may be used to instruct a navigation operation device to perform a corresponding feedback operation. Different navigation feedback instructions may correspond to different feedback operations, etc.

In some embodiments, the feedback operation may include at least one of vibration feedback, sound feedback, movement feedback, force feedback, image feedback, video feedback, etc.

In some embodiments, the content displayed on the display screen may include at least one of an image display interface, a system operation interface, etc. The image display interface may display one or more images. The system operation interface may perform operations on components of the ultrasound imaging system, for example, the operation imaging device, etc.

In some embodiments, the feedback generation module 720 may extract the navigation information in the navigation operation instruction and obtain a current content displayed of the display screen, and generate the navigation feedback instruction based on the navigation information and the content displayed on the display screen.

In some embodiments, the feedback generation module 720 may determine a moving track of the navigation cursor on the display screen by analyzing the navigation information. For each input operation (from starting moving to stopping moving) performed by the user using the navigation operation component (e.g., the navigation operation component 220), the navigation operation device may generate a navigation operation instruction corresponding to the input operation, and the navigation operation instruction may include a plurality of navigation information. Each of the navigation information may include more than one of the information such as a position, a movement direction, a movement distance, a movement speed, etc., and other information of the navigation cursor.

In some embodiments, the feedback generation module 720 may analyze the plurality of navigation information in the navigation operation instruction to form a moving track of the navigation cursor on the display screen by connecting positions of the navigation cursor in each navigation information in sequence according to a time sequence generated by the plurality of navigation information.

In some embodiments, after determining the moving track of the navigation cursor, the navigation feedback instruction may be generated based on the moving track and the content displayed.

In some embodiments, the content displayed may include a region of interest and a region of non-interest. The region of interest/region of non-interest in the content displayed may be at least one of a default, determined based on a pre-input division parameter, automatically recognized based on the content displayed, etc.

In some embodiments, when the display screen includes the image display interface, the region of interest may include an image region pre-selected by the user, or a target image region automatically recognized by the system; and the region of non-interest may include a region other than the region of interest in the image display interface, or a function operation region in the image display interface. In some embodiments, when the content displayed includes a system operation interface, the region of interest may include a function operation region (used to perform operations or functions such as imaging of the ultrasound imaging system); and the region of non-interest may include the region other than the region of interest in the system operation interface.

In some embodiments, the feedback generation module 720 may generate the navigation feedback instruction based on the movement information of the moving track.

In some embodiments, the movement information of the moving track may include whether the moving track passes through a reference line. The feedback generation module 720 may obtain the reference line; in response to that the moving track passes the reference line, a first navigation feedback instruction may be generated. The first navigation feedback instruction may be used to instruct the navigation operation device (e.g., the device 300) or an element of a feedback assembly (e.g., the feedback assembly 230) to generate the feedback operation indicating that the moving track passes the reference line. In some embodiments, the reference line may include an intersection line between the region of interest and the region of non-interest, a boundary line of the display screen, a boundary of the image display interface or the system operation interface, etc.

The reference line being the intersection line between the region of interest and the region of non-interest may be taken as an example for illustration. The feedback generation module 720 may extract the intersection line between the region of interest and the region of non-interest in the content displayed, determine whether there is an intersection point between the moving track of the navigation cursor and the intersection line, and then based on the result of whether there is an intersection point between the moving track of the navigation cursor and the intersection line, determine whether the moving track passes through the intersection line. In response to that there is an intersection point between the moving track and the intersection line, the feedback generation module 720 may determine that the moving track of the navigation cursor passes through the intersection line between the region of interest and the region of non-interest; conversely, if there is no intersection point between the moving track and the intersection line, the feedback generation module 720 may determine that the moving track of the navigation cursor does not pass through the intersection line between the region of interest and the region of non-interest.

In some embodiments, the feedback operation generated based on the first navigation feedback instruction may include generating a resistance force. The resistance force may be applied to the navigation operation component to prevent the user to perform the input operation, i.e., moving the cursor. For example, when the cursor moves to a boundary of the display screen, a great resistance may be fed back, reminding the user that the cursor has reached an edge of the display screen and also preventing the user from moving further. As another example, the cursor may move among different regions of the display screen, and the cursor may enter and exit the different regions of the display screen. When the cursor moves to the boundary of a current region, a slightly greater resistance may be given compared with the resistance when the cursor is inside the region, so as to suggest that the cursor is likely to be moved out of the current region. At this time, the user may choose to continue to move out of the current region, or to return to the current region.

In some embodiments, the movement information of the moving track may include whether the moving track is far from the region of interest. The feedback generation module 720 may determine, based on a position of each track point of the moving track, whether the moving track is moving far from the region of interest; and in response to that the moving track is moving far from the region of interest, a second navigation feedback instruction may be generated. The second navigation feedback instruction may be used to instruct the navigation operation device (e.g., the device 300) or the element of the feedback assembly (e.g., the feedback assembly 230) to generate the feedback operation to indicate that the moving track is far from the region of interest.

In some embodiments, a plurality of track points may be included on the moving track, and each navigation information included in the navigation operation instruction may correspond to a formation of the track point, the plurality of navigation information may correspond to the plurality of track points, and the plurality of track points may be connected to form the moving track in a sequential manner according to the time sequence in which they are generated. The position of each track point of the moving track may be the position of the navigation cursor in the corresponding navigation information.

In some embodiments, the feedback generation module 720 may obtain the positions of the navigation cursor in the plurality of navigation information forming the moving track as the positions of the corresponding track points in the moving track. As the track points are continuously generated, the feedback generation module 720 may obtain a distance between each track point relative to the region of interest in real time to determine whether the distance between the track point and the region of interest is gradually increasing. In response to that the distance between the track point and the region of interest is increasing, it may be determined that the moving track of the navigation cursor is far from the region of interest; in response to that the distance between the track and the region of interest is not increasing, it may be determined that the moving track of the navigation cursor is not far from the region of interest.

In some embodiments, upon determining that the moving track of the navigation cursor is not far from the region of interest, the feedback generation module 720 may generate the second navigation feedback instruction to instruct the navigation operation device or the element of the feedback assembly to generate the feedback operation. This feedback operation may instruct the moving track to move far from the region of interest.

Figure 6:
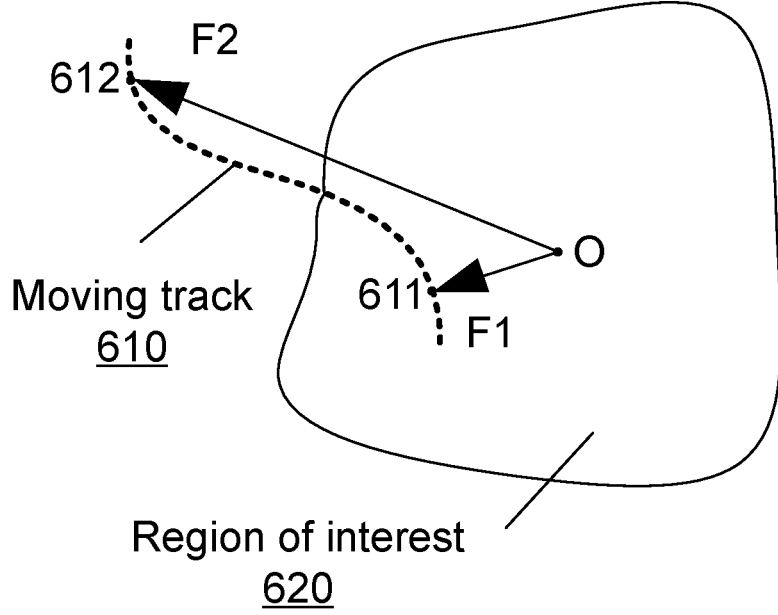
FIG. 6 is a schematic diagram illustrating contents displayed in a display screen according to some embodiments of the present disclosure.

In some embodiments, the feedback generation module 720 may obtain a target direction of a position of the track point relative to the region of interest. Specifically, for each new track point generated, the feedback generation module 720 may obtain the direction of the position of the corresponding track point relative to the region of interest, i.e., the target direction. The target direction may include the direction pointing from a reference position in the region of interest to the track point. Taking FIG. 6 as an example, the target direction of a track point 611 relative to a center point position O of the region of interest 620 is F1; and the target direction of a track point 612 relative to the center point position O of the region of interest 620 is F2.

In some embodiments, after obtaining the target direction of the position of the track point relative to the region of interest, the feedback generation module 720 may generate the second navigation feedback instruction instructing the navigation operation device to move in an opposite direction of the target direction, which causes the navigation cursor to move in the opposite direction of the target direction or causes the user receives a resistance force for operating the navigation operation device. Still taking FIG. 6 as the example, when the navigation cursor moves to the track point 611, the controller 232 may generate the second navigation feedback instruction that instructs the navigation cursor to move in the opposite direction of F1; and when the navigation cursor moves to the track point 612, the controller 232 may generate the second navigation feedback instruction that instructs the navigation cursor to move in the opposite direction of F2.

In some embodiments, a speed of the movement of the navigation operation device in the opposite direction of the target direction may increase as the moving track moves far from the region of interest. Still taking FIG. 6 as an example, when the second navigation feedback instruction indicating that the navigation cursor moves in the opposite direction of F1 is generated at the track point 611, the second navigation feedback instruction may control the navigation operation device to move in the opposite direction of F1 at a speed V1, and if the user continues to control the navigation cursor when the navigation cursor reaches the track point 612, the generated second navigation feedback instruction may control the navigation operation device to move in the opposite direction of F2 at a speed V2 (V2>V1). During the movement of the navigation cursor from the track point 611 to the track point 612, the speed of movement of the corresponding control navigation operation device gradually increases. The speed may either increase linearly or segmentally as the distance between the track point and the region of interest increases. Through the increase of the moving speed of the navigation operation device, the user may obviously feel a current moving state of the navigation operation device, so as to produce a prompt guidance to the user, and then improve a feedback effect to achieve an effective feedback.

In some embodiments, the speed of movement of the corresponding control navigation operation device may be unchanged or gradually decrease as the moving track moves far from the region of interest.

In some embodiments, the feedback operation generated based on the second navigation feedback instruction may include generating the resistance force, the vibration, etc. For example, when the moving track is moving far from the region of interest, the feedback resistance force or the vibration may indicate that the moving track is moving far from the region of interest, and the farther from the region of interest and the faster the moving track is moving away, then the stronger the resistance force or vibration may be.

In some embodiments of the present disclosure, by generating the navigation feedback instructions based on the movement information of the moving track in the region of interest and the region of non-interest, different movement information may correspond to different navigation feedback instructions, thereby instructing the navigation feedback to perform different styles of the feedback operations. In this way, the feedback styles may be enriched, and the users may be provided with different tactile feedback through different feedback styles, which provides the users with an accurate operational guidance, thus implementing a more accurate navigation operation for the users.

In the medical field, the content displayed by the display screen often presents some dynamic objects, for example, a flowing blood, a beating heart, etc. For the dynamic objects of the content displayed, the corresponding dynamic feedback may be implemented by the navigation feedback instruction. Taking a Doppler mode of the ultrasound device as an example, the Doppler mode may often be used in a scene of rapid movement of the blood flow, a tissue, etc. In some embodiments, the controller 232 may utilize a vibration or movement to simulate a tactile sensation of the blood flow, and may reflect a flowing speed and a flow volume of the blood, etc., through a frequency and amplitude of the vibration or movement. For example, a higher vibration frequency may reflect a faster blood flow, and a higher vibration amplitude may reflect a higher flow volume.

In some embodiments, the controller 232 may determine an end position of the moving track in the content displayed. The end position of the moving track may include the position of the navigation cursor in a plurality of attribute information that is ranked last according to a time sequence among the plurality of attribute information forming the moving track, etc. In some embodiments, the controller 232 may directly obtain the position of the navigation cursor in the attribute information corresponding to the latest time as the end position of the moving track in the content displayed.

In some embodiments, the controller 232 may obtain motion information of the displayed object at the end position in the content displayed. When a dynamic object is included in the content displayed, the display object may also accordingly include the motion information, such as a direction of motion, an acceleration, a speed, etc. of the object. In some embodiments, the controller 232 may perform an image recognition of the displayed content to determine a region to which each object in the content displayed belongs, and then match the end position of the moving track with the region to which each object belongs to determine a target region the end position of the moving track is located, and then obtain the motion information of the object the target region includes.

In some embodiments, after obtaining the motion information, the controller 232 may generate a third navigation feedback instruction based on the motion information. The third navigation feedback instruction may be used to instruct the navigation operation device (e.g., the device 300) to generate a motion consistent with the motion information of the object. For example, if the object at the end position of the motion track is the flowing blood, the controller 232 may obtain the motion information of the blood region, i.e., a flow direction and a flow speed of the blood in the region, and generate the corresponding third navigation feedback instruction to instruct the navigation operation device to perform a movement with the flow direction as the movement direction and the flow speed as the movement speed. As another example, if the object at the end position of the motion track is the beating heart, the feedback generation module 720 may obtain the motion information of the heart region, i.e., a beating period and a beating intensity of the heart, and generate the corresponding third navigation feedback instruction to instruct the navigation operation device to perform a vibratory motion with the beating period as a vibration period and the beating intensity as an amplitude intensity. As a further example, when the region of interest is determined to be the heart, the third navigation feedback instruction may instruct the generation of four vibration feedback, each vibration having a duration of 2 seconds and an interval of 1 second. As still another example, when the region of interest is determined to be the brain, the third navigation feedback instruction may instruct two vibration feedback to be generated, each vibration having a duration of 5 seconds and an interval of 3 seconds.

In some embodiments of the present disclosure, for the dynamic display object in the content displayed, by generating the navigation feedback instruction based on the motion information of the display object at the end position of the moving track in the content displayed, the navigation operation device may be instructed to generate a motion consistent with the motion information of the display object. In this way, the dynamic feedback on the dynamic display object in the content displayed may be implemented, so as to enable the user to feel the motion state of the display object more directly based on the motion of the navigation operation device, thus enhancing an interaction experience of the user.

An M-mode (i.e., the motion mode) of the ultrasound imaging device allows an observation of the movement of human organs and/or tissues, and may be mainly used for a cardiac ultrasound diagnosis, etc. In particular, the cardiac ultrasound diagnosis may require a selection of feature points, for example, an apex, a mitral valve, and a ventricular wall edge, etc. In some embodiments, the feedback generation module 720 may generate a fourth navigation feedback instruction.

In some embodiments, the feedback generation module 720 may determine the region of interest based on the navigation information. Specifically, the feedback generation module 720 may determine the moving track based on the navigation information, and then determine, based on the moving track and the content displayed, information such as whether a current region is the region of interest and a type of the region of interest. For example, when the content displayed includes an image display interface, if the moving track passes through organs such as a brain, the heart, etc. shown on the display screen, the feedback generation module 720 may determine these organs as the regions of interest.

In some embodiments, during the cardiac ultrasound diagnosis, the feedback generation module 720 may obtain a position of the selected feature point in real time based on the moving track and the content displayed by various means (e.g., image recognition, AI technology, etc.) to form a real-time motion track of the feature point.

In some embodiments, the feedback generation module 720 may generate the fourth navigation feedback instruction based on the feature of the region of interest. The fourth navigation feedback instruction may be used to instruct the navigation operation device or the element of the feedback assembly to generate a feedback operation to indicate the feature of the region of interest. The feature of the region of interest may include the softness or hardness, the elasticity, etc. In some embodiments, the feedback generation module 720 may identify the region of interest from the ultrasound image and determine the feature of the region of interest based on the identified region of interest. For example, the feedback generation module 720 may identify the type of the region of interest (e.g., a node, a polyp, etc.), and generate the fourth navigation feedback instruction based on the type of the region of interest. As another example, the probe of the ultrasound device may apply a force on the region of interest, and a reaction force may be generated and received by the probe, the probe may transmit the reaction force to the feedback generation module 720. The feedback generation module 720 may generate the fourth navigation feedback instruction based on the reaction force. The fourth navigation feedback instruction may be configured to drive the feedback assembly to provide a force feedback. For example, the force feedback may provide the reaction force. The reaction force may indicate the softness or hardness, the elasticity, of the region of interest. The smaller the reaction force is, the softer the region of interest may be.

In some embodiments, after obtaining the real-time motion track of the feature point during the cardiac ultrasound diagnosis, the feedback generation module 720 may control the navigation operation component or the element of the feedback assembly to synchronize their motion (i.e., to move and vibrate) according to that motion track, thereby providing a true feedback of the tactile sensation of the heart when the heart is beating.

In some embodiments of the present disclosure, by determining the region of interest based on the navigation information and generating different navigation feedback instructions based on the feature of the region of interest, different feedback may be provided when the motion track passes through different regions of interest, which is helpful for the operation of the user, thus enhancing the user experience.

In some embodiments, when an abnormal state involves during the navigation operation, the feedback generation module 720 may generate a fifth navigation feedback instruction based on a type of the abnormal state. The fifth navigation feedback instruction may be used to instruct the navigation operation device or the element in the feedback assembly to generate the feedback operation to indicate the encounter of the abnormal state. In some embodiments, the abnormal state may include an abnormal result in a measurement (e.g., scanning data), an interface interaction (e.g., click to select, double-click to open, etc.), etc. The feedback operation corresponding to the fifth navigation feedback instruction may include the vibration, the movement, etc.

In 530, the feedback assembly may be controlled to drive, based on the navigation feedback instruction, the navigation operation component, or the element of the feedback assembly to provide the feedback operation. In some embodiments, operation 530 may be performed by the feedback performing module 730.

In some embodiments, after generating the navigation feedback instruction, the feedback generation module 720 may send the generated navigation feedback instruction to the feedback assembly (e.g., the feedback assembly 230, the driving component 303) to control the feedback assembly to drive the navigation operation component (e.g., the navigation operation component 220, the navigation operation component 302), or the element of the feedback assembly to provide the feedback operation. The feedback operation may include one or more of a vibration feedback, a sound feedback, a movement feedback, a force feedback, an image, or a video feedback, etc. When implementing the vibration feedback and/or the force feedback, the element of the feedback assembly may include a vibration motor; when implementing the movement feedback, the element of the feedback assembly may include a motor, a power roller, etc.; when implementing the sound feedback, the element of the feedback assembly may include a speaker, etc.; and when implementing the image or video feedback, the element of the feedback assembly may include a display screen, a VR device, etc.

In some embodiments, if the navigation feedback instruction is used to instruct the navigation operation component to vibrate, the feedback generation module 720 may control the element of the feedback assembly (e.g., the driving component 303) in the navigation operation device to drive the navigation operation component to implement the feedback operation, such as the vibration feedback and/or the force feedback. In some embodiments, when the navigation operation device includes the navigation operation component (e.g., the navigation operation component 302), the feedback generation module 720 may control the feedback assembly (e.g., the driving component 303) in the navigation operation device to drive the navigation operation component to perform a corresponding feedback operation such as the vibration feedback and/or the force feedback.

In some embodiments, if the navigation feedback instruction is used to instruct the navigation operation device (e.g., the device 300) to move, the feedback generation module 720 may control the element of the feedback assembly (e.g., the driving component 303) in the navigation operation device to drive the device to move to achieve the movement feedback. The feedback assembly may include a driving roller, etc. In some embodiments, when the navigation operation device includes the navigation operation component (e.g., the navigation operation component 302), the feedback generation module 720 may control the feedback assembly (e.g., the driving component 303) in the navigation operation device to drive the navigation operation component to rotate for the movement feedback. The feedback assembly may include a motor whose rotating shaft is in a tangential contact with the navigation operation component, the motor may rotate to drive the navigation operation component to rotate.

In some embodiments, the feedback generation module 720 may analyze the navigation feedback instruction to obtain a target parameter for controlling the driving component to control the vibration motor to drive the navigation operation component to vibrate according to the target parameter, or the feedback generation module 720 may calculate an underlying parameter through an algorithm such as a field orientation control (FOC) to control a first motor (e.g., the first motor 3031-1) and a second motor (e.g., the first motor 3031-2) to rotate based on the target parameter through the underlying parameter.

In some embodiments of the present disclosure, the navigation feedback instruction may be generated based on the navigation information in the navigation operation instruction and the content displayed on the display screen, so as to make the navigation operation device perform the corresponding feedback operation based on the navigation feedback instruction. In this way, the feedback of the ultrasound imaging system for the navigation operation may be implemented, thereby providing a good guidance for the user to operate the navigation operation device, improving the convenience of a user interaction, and facilitating the user to realize more accurate navigation operation.

It should be noted that the foregoing description of the process 500 is intended to be exemplary and illustrative only and does not limit the scope of application of the present disclosure. For those skilled in the art, various corrections and changes may be made to the process 500 under the guidance of the present disclosure. However, these corrections and changes remain within the scope of the present disclosure. For example, a plurality of feedback operations such as the vibration and the movement may be performed simultaneously.

Figure 7:
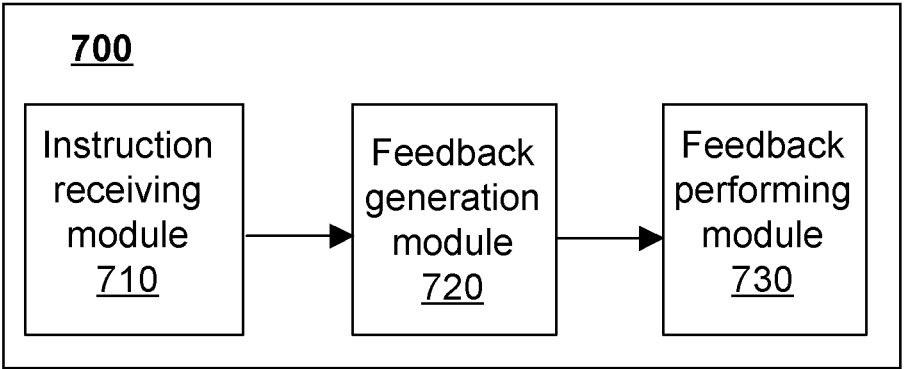
FIG. 7 is a schematic diagram illustrating a feedback assembly for a navigation operation according to some embodiments of the present disclosure.

FIG. 7 is a schematic diagram illustrating a device for performing feedback on a navigation operation according to some embodiments of the present disclosure.

As shown in FIG. 7, a device 700 may include an instruction receiving module 710, a feedback generation module 720, and a feedback performing module 730. In some embodiments, the various modules in the device 700 may be implemented by the processing device 110 and/or the controller 232.

In some embodiments, the instruction receiving module 710 may be configured to receive a navigation operation instruction sent by a navigation operation component (e.g., the navigation operation component 220, the navigation operation component 302). The navigation operation instruction may include navigation information indicating a movement of a navigation cursor on a display screen of an ultrasound imaging system (e.g., the system 100, the system 400).

In some embodiments, the feedback generation module 720 may be configured to generate a navigation feedback instruction based on the navigation operation instruction (e.g., the navigation information or the navigation operation) and a content displayed on the display screen.

In some embodiments, the feedback generation module 720 may analyze the navigation information to determine a moving track of the navigation cursor on the display screen; and generate the navigation feedback instruction based on the moving track and the content displayed.

In some embodiments, the content displayed may include a region of interest and a region of non-interest, and the feedback generation module 720 may generate the navigation feedback instruction based on the movement information of the moving track in the region of interest and the region of non-interest.

In some embodiments, the feedback generation module 720 may extract an intersection line between the region of interest and the region of non-interest; and in response to that the moving track passes the reference line, the feedback generation module 720 may generate a first navigation feedback instruction. The first navigation feedback instruction may be used to instruct the navigation operation device (e.g., the device 300) or an element of the feedback assembly to generate a feedback operation indicating that the moving track passes the reference line In some embodiments, the feedback operation may include at least one of vibration feedback, sound feedback, movement feedback, force feedback, image feedback, video feedback, etc.

In some embodiments, the feedback generation module 720 may determine, based on a position of each track point in a moving track, whether the moving track is far from the region of interest; in response to that the moving track is moving far from the region of interest, the feedback generation module 720 may generate a second navigation feedback instruction. The second navigation feedback instruction may be used to instruct the navigation operation device or the element of the feedback assembly to generate the feedback operation indicating that the moving track is far away from the region of interest.

In some embodiments, the feedback generation module 720 may obtain a target direction of the position of the track point relative to the region of interest; generate the second navigation feedback instruction indicating a movement of the navigation operation device in an opposite direction of the target direction. In some embodiments, a speed of the movement of the navigation operation device in the opposite direction of the target direction may increase as the moving track moves away from the region of interest.

In some embodiments, the feedback generation module 720 may determine an end position of the moving track in the content displayed; obtain motion information of a display object at the end position in the content displayed; and generate a third navigation feedback instruction based on the motion information. The third navigation feedback instruction may be used to instruct the navigation operation device to generate a motion consistent with the motion information of the display object.

In some embodiments, the feedback generation module 720 may determine the region of interest based on the navigation information; generate a fourth navigation feedback instruction based on a feature of the region of interest. The fourth navigation instruction may be used to instruct the navigation operation device or the element of the feedback assembly to generate the feedback operation to indicate the feature of the region of interest.

In some embodiments, the feedback performing module 730 may be configured to control the feedback assembly (the feedback assembly 230, the driving component 303) to drive the navigation operation component, or control the element of the feedback device to provide the feedback according to the navigation operation.

FIG. 8 is a schematic diagram illustrating a navigation operation system according to some embodiments of the present disclosure. A navigation operation system 800 may be referred to as a system 800 in the present disclosure.

As shown in FIG. 8, the system 800 may include a first navigation operation device 810, a second navigation operation device 820, and a driving component 830. In some embodiments, the driving component 830 may be integrated into the second navigation operation device 820 and be a portion of the second navigation operation device 820.

In some embodiments, the first navigation operation device 810 may be configured to perform a first navigation operation on another display screen. In some embodiments, the first navigation operation device 810 may be configured to implement the first navigation operation on the another display screen in a first imaging system (e.g., an ultrasound imaging system (e.g., the system 100, the system 400)). In some embodiments, the first navigation operation device 810 may be the same or similar to the device 300. In some embodiments, the first navigation operation device 810 may be different from the device 300. For example, different from the device 300, the first navigation operation device 810 may not include the driving component. In some embodiments, the another display screen, the first navigation operation device 810, and the first imaging system may be located in the same first geographic range, and a user may be able to perform the first navigation operation at the another display screen through the first navigation operation device 810. As used herein, the same geographic range refers to a region range that is within a field of view of the user.

In some embodiments, the second navigation operation device 820 may be configured to perform a second navigation operation on a display screen. In some embodiments, the second navigation operation device 820 may be configured to implement the second navigation operation on the display screen in a second imaging system (e.g., an ultrasound imaging system (e.g., the system 100, the system 400)). In some embodiments, the second navigation operation device 820 may be the same or similar to the device 200 or the device 300. For example, the second navigation operation device may include a navigation operation component that is same as the navigation operation component of the device 200 or the device 300. In some embodiments, the second navigation operation device 820 may be different from the device 300. For example, different from the device 300, the second navigation operation device 820 may not include the driving component. In some embodiments, the second navigation operation may be performed by the navigation operation component of the second navigation operation device 820. For example, the user may directly operate the navigation operation component of the second navigation operation device 820 to perform the second navigation operation. As another example, the user may control the navigation operation component of the second navigation operation device 820 through an instruction sent remotely to perform the second navigation operation. In some embodiments, the display screen, the second navigation operation device 820, and the second imaging system may be located in the same second geographic range, and the user may be able to perform the second navigation operation on the display screen through the second navigation operation device 810. The first geographic range may be different from the second geographic range. For example, the first geographic range and the second geographic range may be located in different cities, different hospitals, different countries, etc.

In some embodiments, the driving component 830 may be configured to drive the navigation operation component of the second navigation operation device 820 to perform the second navigation operation on the display screen based on the first navigation operation. The navigation information of the first navigation operation on the another display screen and the navigation information of the second navigation operation on the display screen may be the same. The navigation information refers to a content of an image displayed, for example, an organ/tissue, an object pointed by a cursor, a cursor position, a cursor movement status, etc. The driving component 830 and the second navigation operation device 820 may be located in the same second geographic range.

In some embodiments, the first navigation operation device 810 may be connected with the second navigation operation device 820 and the driving component 830 through a wired network and/or a wireless network. The first navigation operation device 810 may transmit the information presenting the first navigation operation to the second navigation operation device 820 and/or the driving component 830. The first navigation operation performed by a user through the first navigation operation device 810 may be synchronized to the second navigation operation device 820. The driving component 830 may drive, based on the first navigation operation, the navigation operation component of the second navigation operation device 820 to perform the second navigation operation on the display screen. The content of the second navigation operation may be the same as the content of the first navigation operation. In some embodiments, the content displayed (i.e., the navigation information) by the display screen based on the second navigation operation may be synchronized to the another display screen, so that the navigation information of the first navigation operation on the another display screen may be the same as the navigation information of the second navigation operation on the display screen for the user to synchronously read a result of the first navigation operation.

In some embodiments, the first navigation operation device 810 and the second navigation operation device 820 may be operated by different users. A first user may operate the first navigation operation device 810, and a second user may operate the second navigation operation device 820. In some embodiments, the navigation operation performed locally by each of the first and second users may be synchronized to the other in real time. For example, the first user may operate the first navigation operation device 810, and the first navigation operation may be synchronized in real time to the second navigation operation device 820, so that the second navigation operation device 820 may perform the second navigation operation that is the same as the first navigation operation. As another example, the second user may operate the second navigation operation device 820, and the second navigation operation may be synchronized in real time to the first operation device 810, so that the first operation device 810 may perform the first navigation operation that is the same as the second navigation operation.

In some embodiments of the present disclosure, a remote navigation operation of the user may be implemented through two navigation operation devices (a local navigation operation device and a remote navigation operation device) and the corresponding display screens, which facilitates the operation of the user, and at the same time, alleviates a problem of insufficient high-quality medical resources.

Figure 9:
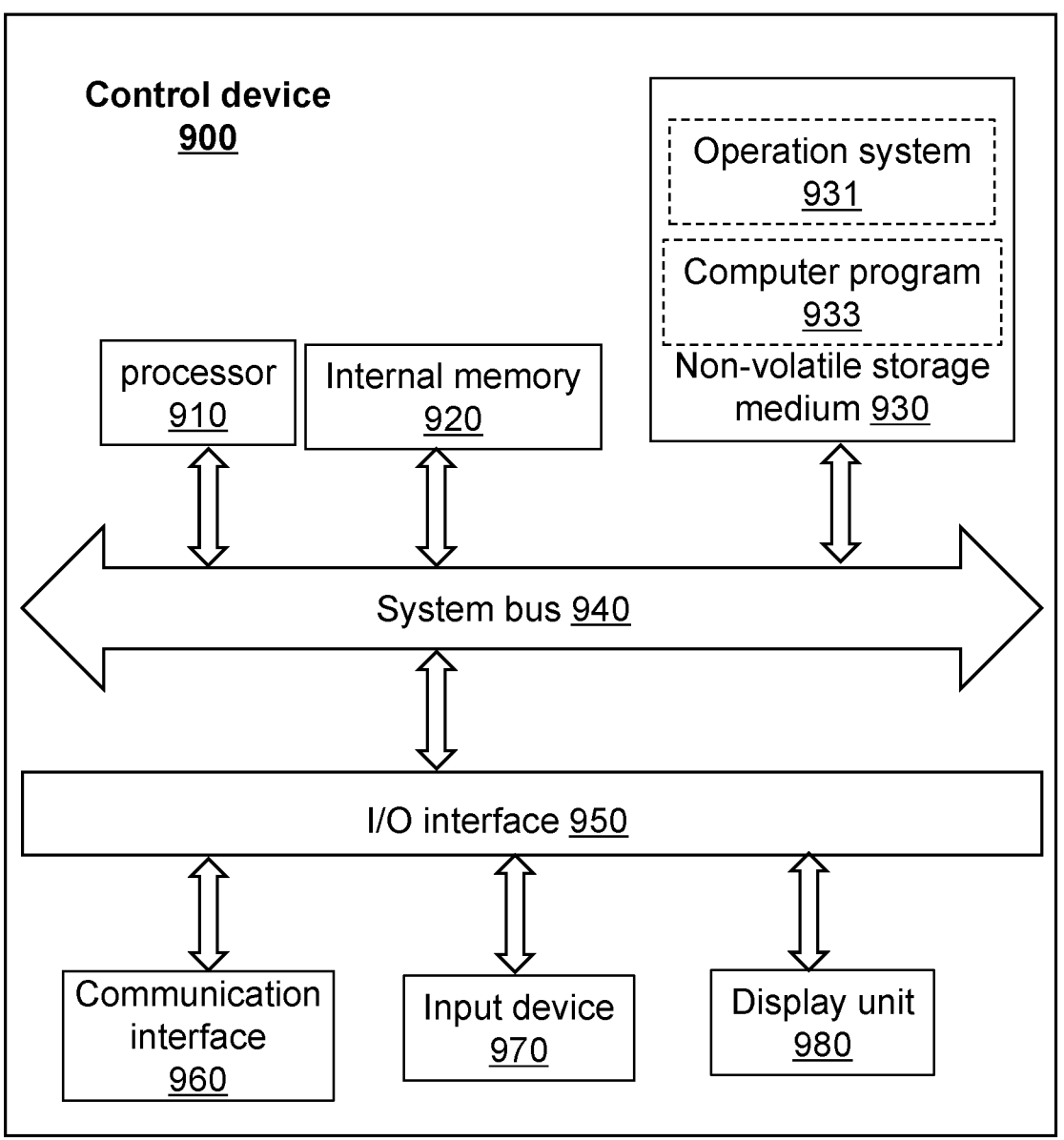
FIG. 9 is a schematic diagram illustrating an exemplary control device of an ultrasound imaging system according to some embodiments of the present disclosure.

FIG. 9 is a schematic diagram illustrating an exemplary control device of an ultrasound imaging system according to some embodiments of the present disclosure. In some embodiments, the system 100 may include a control device 900.

As shown in FIG. 9, the control device 900 may include a processor 910 connected through a system bus 940, a memory (including an internal memory 920 and a non-volatile storage medium 930), a communication interface 950, an input device 970 and a display unit 980. The communication interface 950, the input device 970 and the display unit 980 may be connected to the system bus 940 through the I/O interface 950.

The processor 910 may be configured to provide computing and control capabilities. In some embodiments, the processor 910 may perform the feedback mode of the navigation operation as described in some embodiments of the present disclosure by executing computer instructions (e.g., a computer program 933) in the memory. The non-volatile storage medium 930 may store an operation system 931 and a computer program 933. The internal memory 920 may provide an operation environment for the operation system 931 and the computer program 933 in the non-volatile storage medium 930.

The communication interface 950 may be configured for a wired or wireless communication with an external terminal (e.g., the operation terminal 120, the medical imaging device 130, and the storage device 140). The display unit 980 may be configured to display various types of information such as an interactive interface with a user. The display unit 980 may include various types of display screens, for example, a liquid crystal display screen, an e-ink display screen, a VR display device, etc. The input device 970 may be configured for a user input, and may include various input devices, for example, keys integrated in the device itself, a trackball, or a touch pad, etc., a touch layer covered on the touch screen, an external keyboard, a touch pad or a mouse, etc.

Beneficial effects that may be brought about by the embodiments of the present disclosure include, but are not limited to: (1) in the medical imaging system, a diversified feedback (e.g., the vibration, the movement, etc.) on the user's navigation operation may be implemented by the trackball and other navigation operation components based on the region of interest etc., thereby enhancing the user's experience in the navigation operation, guaranteeing the accuracy of the navigation operation, and thus ensuring a good imaging effect; (2) By adding vibration and other feedbacks to the trackball mouse to prompt the user for the navigation operation, an application scope of the trackball mouse may be extended, and an user interactivity may be improved. It is to be noted that different embodiments may produce different beneficial effects, and in different embodiments, the beneficial effects produced may be any one or a combination of the above, or any other beneficial effect that may be obtained.

The basic concepts have been described above, and obviously, for those skilled in the art, the above disclosure of the invention is only an example, and does not constitute a limitation to the present disclosure. Although not expressly stated here, various modifications, improvements and amendments to the present disclosure may be made by those skilled in the art. Such modifications, improvements, and amendments are suggested in the present disclosure, so such modifications, improvements, and amendments still belong to the spirit and scope of the exemplary embodiments of the present disclosure Meanwhile, the present disclosure uses specific words to describe the embodiments of the present disclosure. For example, "one embodiment", "an embodiment" and/or "some embodiments" means a certain feature, structure or characteristic related to at least one embodiment of the present disclosure. Therefore, it should be emphasized and noted that two or more references to "an embodiment" or "one embodiment" or "an alternative embodiment" in different places in the present disclosure do not necessarily refer to the same embodiment. Further, certain features, structures, or characteristics of one or more embodiments of the present disclosure may be properly combined.

In addition, unless explicitly stated in the claims, the order in which elements and sequences are processed, the use of numbers and letters, or the use of other designations in the present disclosure is not intended to limit the order of the flows and methods thereof. While the foregoing disclosure has discussed by way of various examples some embodiments of the invention that are presently believed to be useful, it should be understood that such detail is for illustrative purposes only and that the appended claims are not limited to the disclosed embodiments, but rather, the claims are intended to cover all modifications and equivalent combinations that fall within the spirit and scope of the embodiments of the present disclosure. For example, although the system assemblies described above may be implemented by hardware devices, they may also be implemented by a software-only solution, such as installing the described system on an existing server or mobile device.

Similarly, it should be noted that in order to simplify the expression disclosed in the present disclosure and help the understanding of one or more embodiments of the present disclosure, in the foregoing description of the embodiments of the present disclosure, sometimes multiple features are combined into one embodiment, drawings or descriptions thereof. However, this method of disclosure does not, however, imply that the subject matter of the application requires more features than are recited in the claims. Rather, the claimed subject matter may lie in less than all features of a single foregoing disclosed embodiment.

In some embodiments, numbers describing the quantity of assemblies and attributes are used. It should be understood that such numbers used in the description of the embodiments use the modifiers "about", "approximately" or "substantially" in some examples to retouch. Unless otherwise stated, the "about", "approximately" or "substantially" indicates that the stated number allows for a variation of ±20%. Accordingly, in some embodiments, the numerical parameters used in the present disclosure and the claims are approximations that can vary depending upon the desired characteristics of individual embodiments. In some embodiments, the numerical parameters should consider the specified significant digits and adopt the general digit reservation method. Although the numerical ranges and parameters used in some embodiments of the present disclosure to confirm the breadth of the scope are approximate values, in specific embodiments, such numerical values are set as precisely as practicable.

The entire contents of each patent, patent application, patent application publication, and other material, such as article, book, specification, publication, document, etc., cited in the present disclosure are hereby incorporated by reference into the present disclosure. Application history documents that are inconsistent with or conflict with the content of the present disclosure are excluded, and documents (currently or later appended to the present disclosure) that limit the broadest scope of the claims of the present disclosure are excluded. It should be noted that if there is any inconsistency or conflict between the descriptions, definitions, and/or terms used in the accompanying materials of the present disclosure and the contents thereof, the descriptions, definitions and/or terms used in the present disclosure shall prevail.

Finally, it should be understood that the embodiments described in the present disclosure are only used to illustrate the principles of the embodiments of the present disclosure. Other deformations may further belong to the scope of the present disclosure. Therefore, by way of example and not limitation, alternative configurations of the embodiments of the present disclosure may be considered consistent with the teachings of the present disclosure. Accordingly, the embodiments of the present disclosure are not limited to the embodiments explicitly introduced and described in the present disclosure.

What is claimed is:

1. An ultrasound imaging system, comprising:
a navigation operation device including
a supporting component;
a navigation operation component configured to perform a navigation operation on a display screen; and
a feedback assembly configured to drive, based on the navigation operation, the navigation operation component to provide a feedback on the navigation operation, wherein the feedback assembly includes a controller, and the controller is configured to:
increase a speed of a reverse movement of the navigation operation device relative to a target direction as a moving track of the navigation cursor on the display screen moves away from a region of interest, wherein the target direction is a direction of a position of a track point relative to the region of interest.

2. The system of claim 1, wherein the feedback assembly includes a driving component, the driving component being configured to drive the navigation operation component to provide the feedback according to the navigation operation.

3. The system of claim 2, the driving component including at least two motors and a driving circuit, wherein each of the at least two motors includes a rotating shaft, and the driving circuit is configured to drive the at least two motors to rotate, the rotating shaft being connected with the navigation operation component.

4. The system of claim 1, the controller being further configured to:
receive a navigation operation instruction sent by the navigation operation component, wherein the navigation operation instruction includes navigation information indicating that the navigation cursor moves on the display screen of the ultrasound imaging system;
generate a navigation feedback instruction based on the navigation information and a content displayed on the display screen; and
control the feedback assembly to drive, based on the navigation feedback instruction, the navigation operation component to provide a feedback operation.

5. The system of claim 4, the feedback operation including at least one of vibration feedback, movement feedback, or force feedback.

6. The system of claim 4, the generating a navigation feedback instruction based on the navigation information and a content displayed on the display screen comprising:
determining the moving track of the navigation cursor on the display screen by analyzing the navigation information; and
generating, based on the moving track and the content, the navigation feedback instruction.

7. The system of claim 6, wherein the content includes the region of interest and a region of non-interest, and the generating, based on the moving track and the content, the navigation feedback instruction comprises:
generating, based on motion information of the moving track in the region of interest and the region of non-interest, the navigation feedback instruction.

8. The system of claim 7, wherein the generating, based on motion information of the moving track in the region of interest and the region of non-interest, the navigation feedback instruction comprises:
obtaining a reference line; and
in response to that the moving track passes the reference line, generating a first navigation feedback instruction, wherein the first navigation feedback instruction is used to instruct the navigation operation device to generate the feedback operation indicating that the moving track passes the reference line.

9. The system of claim 7, wherein the generating, based on motion information of the moving track in the region of interest and the region of non-interest, the navigation feedback instruction comprises:

determining whether the moving track is far from the region of interest based on a position of each track point in the moving track; and in response to that the moving track is far from the region of interest, generating a second navigation feedback instruction, wherein the second navigation feedback instruction is used to instruct the navigation operation device to generate the feedback operation indicating that the moving track is far away from the region of interest.

10. The system of claim 9, wherein the generating a second navigation feedback instruction comprises:

obtaining the target direction of the position of the track point relative to the region of interest; and generating the second navigation feedback instruction indicating the reverse movement of the navigation operation device relative to the target direction.

11. The system of claim 6, the generating, based on the moving track and the content, the navigation feedback instruction comprising:

determining an end position of the moving track in the display content;

obtaining motion information of the displayed object at the end position in the displayed content; and generating, based on the motion information, a third navigation feedback instruction, wherein the third navigation feedback instruction is used to instruct the navigation operation device to generate a motion consistent with the motion information of the displayed object.

12. The system of claim 5, the generating a navigation feedback instruction based on the navigation information and a content displayed on the display screen comprising:

determining, based on the navigation information, the region of interest; and generating, based on a feature of the region of interest, a fourth navigation feedback instruction, the fourth navigation instruction being used to instruct the navigation operation device to generate the feedback operation indicating the feature of the region of interest.

13. The system of claim 1, wherein the feedback on the navigation operation includes providing a resistance force or a driving force on the navigation operation component for adjusting a previous resistance force of the navigation operation.

14. The system of claim 1, further comprising:

another navigation operation device configured to perform a first navigation operation on another display screen, wherein the feedback assembly is configured to cause, based on the first navigation operation, the navigation operation component to perform a second navigation operation on the display screen, navigation information of the first navigation operation on the another display screen is the same as navigation information of the second navigation operation on the display screen.

15. A navigation operation device, comprising:

a supporting component, a navigation operation component and a driving component, wherein the navigation operation component and the driving component are installed on the supporting component;

the navigation operation component moves driven by the driving component, so as to perform a navigation operation on a display screen of an ultrasonic imaging system; and the driving component includes one or more motors and a driving circuit, wherein the one or more motors include one or more rotating shafts, the one or more rotating shafts are disposed in contact with the navigation operation component, the driving circuit is connected to the one or more motors; and the driving circuit is configured to drive the one or more motors to rotate.

16. The device of claim 15, the navigation operation component including a trackball.

17. The device of claim 15, the one or more motors including a first motor and a second motor; wherein a rotating shaft of the first motor is disposed in contact with the navigation operation component along a first direction, and a rotating shaft of the second motor is disposed in contact with the navigation operation component along a second direction; the first direction and the second direction being different directions.

18. A method for navigation implemented by an ultrasound imaging system including a navigation operation device, the method comprising:

receiving a navigation operation instruction sent by a navigation operation component of the navigation operation device, wherein the navigation operation instruction includes navigation information indicating that a navigation cursor moves on a display screen of the ultrasound imaging system;

generating a navigation feedback instruction based on the navigation information; and controlling a feedback assembly of the navigation operation device to drive, based on the navigation feedback instruction, the navigation operation component to provide a feedback operation, including:

increasing a speed of a reverse movement of the navigation operation device relative to a target direction as a moving track of the navigation cursor on the display screen moves away from a region of interest, wherein the target direction is a direction of a position of a track point relative to the region of interest.

19. The system of claim 2, wherein the driving component includes at least three motors, and the at least three motors are configured to realize a movement in x-axis, y-axis, and z-axis directions in a 3D space to feedback a 3D position change on a 3D display device.

20. The device of claim 15, further comprising a magnetic field sensor disposed on each motor of the one or more motors, the magnetic field sensor being configured to detect a rotation state of the each motor of the one or more motors.

* * * * *